(12) United States Patent
Chobotov

(10) Patent No.: US 9,724,186 B2
(45) Date of Patent: Aug. 8, 2017

(54) ENDOVASCULAR GRAFT FOR ANEURYSMS INVOLVING MAJOR BRANCH VESSELS

(71) Applicant: TriVascular, Inc., Santa Rosa, CA (US)

(72) Inventor: Michael V. Chobotov, Santa Rosa, CA (US)

(73) Assignee: TriVascular, Inc., Santa Rosa, CA (US)

( * ) Notice: Subject to any disclaimer, the term of this patent is extended or adjusted under 35 U.S.C. 154(b) by 282 days.

(21) Appl. No.: 14/050,835

(22) Filed: Oct. 10, 2013

(65) Prior Publication Data

US 2014/0100650 A1    Apr. 10, 2014

Related U.S. Application Data

(60) Provisional application No. 61/711,797, filed on Oct. 10, 2012, provisional application No. 61/750,850, filed on Jan. 10, 2013.

(51) Int. Cl.
*A61F 2/06* (2013.01)
*A61F 2/07* (2013.01)

(52) U.S. Cl.
CPC .......... *A61F 2/07* (2013.01); *A61F 2002/061* (2013.01); *A61F 2002/067* (2013.01);
(Continued)

(58) Field of Classification Search
CPC .......... A61F 2002/061; A61F 2002/067; A61F 2002/077
(Continued)

(56) References Cited

U.S. PATENT DOCUMENTS

| 6,176,849 B1 | 1/2001 | Yang et al. |
| 6,524,336 B1 | 2/2003 | Papazolgou et al. |

(Continued)

FOREIGN PATENT DOCUMENTS

| NO | 2013/025493 A1 | 2/2013 |
| WO | 2005/112823 A1 | 12/2005 |

(Continued)

OTHER PUBLICATIONS

Giovanni Torsello et al., "Breaking Barriers: Expanding the EVAR Population", Supplement to Endovascular Today, Nov. 2010, pp. 16-18.
(Continued)

*Primary Examiner* — David Isabella
*Assistant Examiner* — Christine Nelson
(74) *Attorney, Agent, or Firm* — Hoffmann & Baron, LLP

(57) ABSTRACT

Systems and methods for treating diseased bodily lumens involving branched lumen deployment sites include a main graft or stent-graft deployable in a main artery and a vent device or stent-graft deployable in a branch artery to maintain blood flow through the main artery and from the main artery to the branch artery. Systems and methods for treating diseased bodily lumens involving branched lumen deployment sites may also include a main graft or stent-graft deployable in the main artery, a chimney graft or stent-graft deployable in both branch artery and the main artery to the branch artery and a gutter-sealing device associated with the chimney graft to prevent flow of blood among the chimney graft, the main graft and a wall of the main artery.

8 Claims, 17 Drawing Sheets

(52) U.S. Cl.
CPC . *A61F 2002/077* (2013.01); *A61F 2210/0085* (2013.01); *A61F 2250/0003* (2013.01); *A61F 2250/0069* (2013.01)

(58) Field of Classification Search
USPC ........................................................ 623/1.35
See application file for complete search history.

(56) References Cited

U.S. PATENT DOCUMENTS

| | | |
|---|---|---|
| 6,610,035 B2 | 8/2003 | Yang et al. |
| 6,673,103 B1 | 1/2004 | Golds et al. |
| 6,958,212 B1 | 10/2005 | Hubbell et al. |
| 7,090,693 B1 | 8/2006 | Chobotov et al. |
| 7,147,660 B2 | 12/2006 | Chobotov et al. |
| 7,147,661 B2 | 12/2006 | Chobotov et al. |
| 7,150,758 B2 | 12/2006 | Kari et al. |
| 7,744,912 B1 | 6/2010 | Hubbell et al. |
| 2002/0058987 A1 | 5/2002 | Butaric et al. |
| 2005/0228484 A1 | 10/2005 | Stephens et al. |
| 2006/0222596 A1 | 10/2006 | Askari et al. |
| 2006/0224232 A1 | 10/2006 | Chobotov |
| 2006/0233990 A1 | 10/2006 | Humphrey et al. |
| 2006/0233991 A1 | 10/2006 | Humphrey et al. |
| 2009/0099649 A1 | 4/2009 | Chobotov et al. |
| 2012/0041544 A1 | 2/2012 | Wolf |
| 2013/0103135 A1 | 4/2013 | Vinluan |
| 2013/0166010 A1 | 6/2013 | Vad |
| 2014/0005765 A1 | 1/2014 | Hamer et al. |

FOREIGN PATENT DOCUMENTS

| | | |
|---|---|---|
| WO | 2008/021557 A1 | 2/2008 |
| WO | 2008112415 A2 | 9/2008 |
| WO | 2009/046372 A2 | 4/2009 |
| WO | 2009046372 A2 | 4/2009 |
| WO | 2011/158045 A1 | 12/2011 |

OTHER PUBLICATIONS

Konstantinos P Donas et al., "Use of Abdominal Chimney Grafts Is Feasible and Safe: Short-term Results", J. Endovasc. Ther., vol. 17, 2012, pp. 589-593.

Tomas Ohrlander et al., "The Chimney Graft: A Technique for Preserving or Rescuing Aortic Branch Vessels in Stent-Graft Sealing Zones", J. Endovasc. Ther., vol. 15, 2008, pp. 427-432.

U.S. Appl. No. 13/803,037 to Jenine S. Vinluan et al., filed Mar. 14, 2013, entitled "Low Profile Stent Graft and Delivery System".

U.S. Appl. No. 13/803,046 to Sarah Young et al., filed Mar. 14, 2013, entitled "Advanced Kink Resistant Stent Graft".

U.S. Appl. No. 13/803,033 to Michael V. Chobotov et al., filed Mar. 14, 2013, entitled "Low Profile Stent Graft and Delivery System".

V. Suominen et al., "Fenestrated and Chimney Endografts for Juxtzrenal Aneurysms: Early and Midterm Results", Scandinavian Journal of Surgery, vol. 102, 2013, pp. 182-188.

PCT Invitation to Pay Additional Fees with a Partial PCT Search Report, dated Jan. 17, 2014.

EPO Office Action, Application No. 13 780 282.3, dated Aug. 5, 2016.

ENDOVASCULAR GRAFT FOR ANEURYSMS INVOLVING MAJOR BRANCH VESSELS

CROSS-REFERENCE TO RELATED APPLICATIONS

This application claims the benefit of U.S. Provisional Application Nos. 61/711,797, filed Oct. 10, 2012, and 61/750,850, filed Jan. 10, 2013, the contents of all of which are incorporated herein by reference.

FIELD OF THE INVENTION

The present invention relates to endovascular graft systems for aneurysms involving major branch vessels. In particular, the present invention relates to a combination of an endovascular device, such as a chimney graft or a luminal vent device, with a main graft for treating aneurysms involving major branch vessels while avoiding fenestrations or integrated graft appendages in the main graft.

BACKGROUND OF THE INVENTION

The present invention relates to a system for the treatment of disorders of the vasculature, particularly aneurysms. An aneurysm is a medical condition indicated generally by an expansion and weakening of the wall of an artery of a patient. Aneurysms can develop at various sites within a patient's body. Thoracic aortic aneurysms (TAAs) or abdominal aortic aneurysms (AAAs) are manifested by an expansion and weakening of the aorta which is a serious and life threatening condition for which intervention is generally indicated. Existing methods of treating aneurysms include invasive surgical procedures with graft replacement of the affected vessel or body lumen or reinforcement of the vessel with a graft.

Surgical procedures to treat aneurysms can have relatively high morbidity and mortality rates due to the risk factors inherent to surgical repair of this disease, as well as long hospital stays and painful recoveries. Due to the inherent risks and complexities of surgical repair of aortic aneurysms, endovascular repair has become a widely used alternative therapy, most notably in treating AAAs. Early work in this field is exemplified by Lawrence, Jr. et al. in "Percutaneous Endovascular Graft: Experimental Evaluation", Radiology (May 1987) and by Mirich et al. in "Percutaneously Placed Endovascular Grafts for Aortic Aneurysms: Feasibility Study," Radiology (March 1989). Commercially available endoprostheses for the endovascular treatment of AAAs include the Endurant® stent-graft system manufactured by Medtronic, Inc. of Minneapolis, Minn., the Zenith® stent-graft system sold by Cook, Inc. of Bloomington, Ind., the PowerLink® stent-graft system manufactured by Endologix, Inc. of Irvine, Calif., and the Excluder® stent-graft system manufactured by W.L. Gore & Associates, Inc. of Newark, Del. A commercially available stent-graft for the treatment of TAAs is the TAG™ system manufactured by W.L. Gore & Associates, Inc.

In order for aortic endografts to be applied to more patients, their ability to address aneurysms that involve major branch vessels (e.g., left subclavian for thoracic, renals for abdominal, SMA and celiac for thoraco-abdominal) is helpful. One common approach has been through the use of graft fenestrations combined with separate stent-grafts or stents deployed within the branch vessel and through the graft fenestrations (often flared via ballooning to secure the junction). Another technique has been the use of branched endografts in which appendages (branches) are integrated into the main graft.

Both of these approaches have, however, required custom made endografts, with the fenestrations located at the positions of the patient's branch vessels, or for branched grafts, the branches are similarly custom-positioned during device manufacture. These techniques also increase procedural time and complexity significantly and run the risk of inadvertent branch vessel coverage, which can lead to emergent surgical conversion.

More recent approaches are aimed at allowing off the shelf devices to be used. These devices have pre-made fenestrations in a portion of the graft that is unsupported and has redundant material that allows the fenestrations to be moved a limited amount relative to the main graft to allow for the patient to patient variability in branch vessel locations.

Other concepts have included burning or boring fenestrations via access through the branch vessel into the endograft post deployment, but no such approach has been adopted with a commercial as of yet.

Yet another technique is the use of chimney (and/or "snorkel" at the distal end) grafts in combination with a conventional endograft. These separate chimney stent-grafts preserve the branch vessel's patency and typically are positioned between the aortic wall and main endograft, with their other end projecting beyond the edge of the main graft. The chimney is positioned in the body before the main graft is deployed, so if difficulty is encountered in chimney deployment, the chimney may be repositioned and/or redeployed before deployment of the main endograft. In contrast, with fenestrated devices the main device is deployed before access to the branch vessels is completed, which contributes to procedural and device complexity.

Several clinical studies in this context have been described in the literature (see, e.g., Giovanni Torsello et al., "Breaking Barriers: Expanding the EVAR Population", Supplement to Endovascular Today, November 2010, pages 16-18 (using Medtronic Endurant® peripheral stent-grafts)). The challenge in many of these cases is that the round cross section peripheral stent-graft typically used for the branch vessel can pose a sealing challenge for the main stent-graft. Two "gutters", or areas of potential blood leakage, are typically left behind, since the main graft cannot conform fully to the round cross section chimney (which may ovalize somewhat) yet must be stiff enough to resist collapse and prevent branch vessel occlusion. Such blood leakage, if it occurs, can result in clinical problems and even failure of the endograft in performing its task of excluding the aneurysm into which it is deployed.

SUMMARY OF THE INVENTION

The present invention is directed to systems and methods for treating diseased bodily lumens involving branched lumen deployment sites. Blood flow through a main artery and from the main artery to a branch artery is maintained with the blood leakage problems, i.e., "gutters".

In one embodiment, an endovascular system for deployment at branched arteries comprises a main tubular graft deployable within a main artery comprising: a proximal open end, an opposed open distal end and a circumferential sealing member disposed at a location near the proximal end, defining a proximal graft collar portion disposed between the proximal end of the graft and the circumferential sealing member; and an anchoring member securably attached to the proximal graft collar portion, where at least a portion of the anchoring member is disposed beyond the proximal end of the main graft; a vent device deployable within a branch artery branched from the main artery comprising: a main body having an open and an opposed proximal end, the proximal end comprising an open-cage, lattice structure having an atraumatic end; where, when the main graft is deployed within the main artery, the graft collar portion covers or occludes at least a portion of the branch artery, and where, when vent device is deployed within the branch artery, the atraumatic end of the open-cage, lattice structure pushes the graft collar away from a wall of the main artery to provide fluid communication for blood flow from the main artery through the vent device and into the branch artery. The main tubular graft may be an inflatable graft and the circumferential sealing member may be a circumferential inflatable cuff. The open-cage, lattice structure of the vent device may comprise at least two wires. These at least two wires may be curved at an apex, defining the atraumatic end.

In another embodiment, a method for providing blood flow at branched arteries comprises the steps of providing a main tubular graft deployable within a main artery comprising: a proximal open end, an opposed open distal end and a circumferential sealing member disposed at a location near the proximal end, defining a proximal graft collar portion disposed between the proximal end of the graft and the circumferential sealing member; and an anchoring member securably attached to the proximal graft collar portion, where at least a portion of the anchoring member is disposed beyond the proximal end of the main graft; providing a vent device deployable within a branch artery branched from the main artery comprising: a main body having an open and an opposed proximal end, the proximal end comprising an open-cage, lattice structure having an atraumatic end; deploying the vent device within the branch artery; deploying the main graft within the main artery such that the graft collar portion covers or occludes at least a portion of the branch artery; where the atraumatic end of the open-cage, lattice structure pushes the graft collar away from a wall of the main artery to provide fluid communication for blood flow from the main artery through the vent device and into the branch artery. The main tubular graft may be an inflatable graft and the circumferential sealing member may be a circumferential inflatable cuff. The open-cage, lattice structure of the vent device may comprise at least two wires. These at least two wires may be curved at an apex, defining the atraumatic end.

In another embodiment, an endovascular system for deployment at branched arteries comprises a chimney graft having a proximal portion with a proximal open end deployable within a main artery and an opposed distal portion with a distal open end deployable within a branch artery branched from the main artery; and a main tubular graft deployable within the main artery and comprising a proximal open end and an opposed open distal end, the proximal and distal ends defining a tubular graft wall therein between; where, when deployed, a proximal portion of the tubular graft wall spans the branch artery; and where, when deployed, the distal portion of the chimney graft is disposed within the branch artery; where, when deployed, the proximal portion of the chimney graft is disposed within the main artery such that the proximal end of the chimney graft is about adjacent to or extends beyond the proximal end of the main tubular graft; the endovascular system further comprising a gutter-sealing device associated with the proximal portion of the chimney graft to prevent flow of blood among the chimney graft, the main graft and a wall of the main artery; and where, when deployed, the chimney graft provides fluid communication for blood flow from the main artery to the branch artery. The main graft may be an inflatable graft having a proximal circumferential inflatable cuff for sealing the main graft around at least a portion of wall of the main artery. The main graft may further comprise a stent, thereby defining a main stent-graft. The chimney graft may further comprise a stent, thereby defining a chimney stent-graft.

The gutter-sealing device may be disposed about at least a portion of the proximal portion of the chimney graft.

The gutter-sealing device may comprise elongate strips of graft material extending from the proximal portion of the chimney graft for promoting thrombosis to occlude space within the main artery among the chimney graft, the main graft and wall of the main artery.

The gutter-sealing device may comprise a second graft or a sandwich wing graft having a wall with opposed elongate side or wing portions to occupy space within the main artery among the chimney graft, the main graft and wall of the main artery; where the second or sandwich wing graft further comprises a closed distal end, closed off with graft material, and an opposed proximal end. The opposed proximal end of the second or sandwich wing graft may be an open end. The opposed proximal end of the second or sandwich wing graft may be a closed end, i.e., closed off with graft material. The wall of the second or sandwich wing graft may further comprise a metallic support frame disposed within, under or over the wall of the second or sandwich wing. The second or sandwich wing graft may be circumferentially rotatable about the proximal portion of the chimney graft so that the second or sandwich wing graft is alignable between main tubular graft and the wall of the main artery. The second or sandwich wing graft may be secured about the proximal portion of the chimney graft. The proximal portion of the chimney graft and the distal portion of the chimney graft may be twistable relative to one and the other so that the second or sandwich wing graft is alignable between main tubular graft and the wall of the main artery.

The gutter-sealing device may comprise a concentric graft concentrically disposed about the proximal portion of the chimney graft, where the concentric graft is inflatable with an inflation material, such that, upon inflation of the concentric graft with the inflation material, the concentric graft conforms to occlude space within the main artery among the chimney graft, the main graft and wall of the main artery.

In another embodiment, an endovascular system for deployment at branched arteries may comprise: a bifurcated chimney graft having a distal main body with a distal open end and two opposed proximal leg portions each having a proximal open end, where the two opposed proximal leg portions are deployable within a main artery and the distal main body is deployable within a branch artery branched from the main artery; and a main tubular graft deployable within the main artery and comprising a proximal open end and an opposed open distal end, the proximal and distal ends defining a tubular graft wall therein between; where, when deployed, a proximal portion of the tubular graft wall spans the branch artery; and where, when deployed, the distal main body of the bifurcated chimney graft is disposed within the branch artery; where, when deployed, the two opposed proximal leg portions of the bifurcated chimney graft are disposed within the main artery such that the proximal ends of the two opposed proximal leg portions of the bifurcated chimney graft are about adjacent to or extends beyond the proximal end of the main tubular graft; where, when deployed, the two opposed proximal leg portions of the bifurcated chimney graft substantially conform to occlude space within the main artery among the bifurcated chimney graft, the main graft and wall of the main artery; and where, when deployed, the bifurcated chimney graft provides fluid communication for blood flow from the main artery to the branch artery. When deployed, the two opposed proximal leg portions of the bifurcated chimney graft may self-align to occlude space within the main artery among the bifurcated chimney graft, the main graft and wall of the main artery. When deployed, the two opposed proximal leg portions of the bifurcated chimney may be D-shaped. The two opposed proximal leg portions of the bifurcated chimney may be D-shaped prior to deployment. The main graft may be an inflatable graft having a proximal circumferential inflatable cuff for sealing the main graft around at least a portion of wall of the main artery. The main graft may further comprise a stent, thereby defining a main stent-graft. The bifurcated chimney graft may further comprise a stent, thereby defining a bifurcated chimney stent-graft.

In another embodiment, an endovascular system for deployment at branched arteries may comprise: a chimney graft having a proximal portion with a proximal open end deployable within a main artery and an opposed distal portion with a distal open end deployable within a branch artery branched from the main artery, where the proximal portion is triangular shaped and the distal portion is tubular shaped, and where the triangular shaped proximal portion of the chimney graft and the distal portion of the chimney graft are rotatably twistable with respect to one and the other; and a main tubular graft deployable within the main artery and comprising a proximal open end and an opposed open distal end, the proximal and distal ends defining a tubular graft wall therein between; where, when deployed, a proximal portion of the tubular graft wall spans the branch artery; and where, when deployed, the distal portion of the chimney graft is disposed within the branch artery; where, when deployed, the triangular shaped proximal portion of the chimney graft is disposed within the main artery such that the proximal end of the triangular shaped proximal portion of the chimney graft is about adjacent to or extends beyond the proximal end of the main tubular graft; where, when deployed, the triangular shaped portion of the chimney graft alignable between main tubular graft and the wall of the main artery to substantially conform and to occlude space within the main artery among the chimney graft, the main graft and wall of the main artery; and where, when deployed, the chimney graft provides fluid communication for blood flow from the main artery to the branch artery. When deployed, the triangular shaped portion of the chimney graft may self-align to occlude space within the main artery among the chimney graft, the main graft and wall of the main artery. The chimney graft may further comprise a discontinuity between the triangular shaped proximal portion of the chimney graft and the distal portion of the chimney graft so that the triangular shaped portion of the chimney graft can rotate or flip with respect to the distal portion of the chimney graft. The main graft may be an inflatable graft having a proximal circumferential inflatable cuff for sealing the main graft around at least a portion of wall of the main artery. The main graft may further comprise a stent, thereby defining a main stent-graft. The chimney graft may further comprise a stent, thereby defining a chimney stent-graft.

In another embodiment, a method for providing blood flow at branched arteries comprises the steps of: providing a chimney graft having a proximal portion with a proximal open end deployable within a main artery and an opposed distal portion with a distal open end deployable within a branch artery branched from the main artery, the chimney graft further comprising a gutter-sealing device associated with or integral with the proximal portion of the chimney graft; providing a main tubular graft deployable within the main artery and comprising a proximal open end and an opposed open distal end, the proximal and distal ends defining a tubular graft wall therein between; deploying the distal portion of the chimney graft within the branch artery; deploying the proximal portion of the chimney graft within the main artery; deploying a proximal portion of the tubular graft wall until it spans the branch artery; where the proximal end of the chimney graft is about adjacent to or extends beyond the proximal end of the main tubular graft; where, when deployed, the gutter-sealing device prevents flow of blood among the chimney graft, the main graft and a wall of the main artery; and where, when deployed, the chimney graft provides fluid communication for blood flow from the main artery to the branch artery.

DETAILED DESCRIPTION OF THE INVENTION

Figure 1:
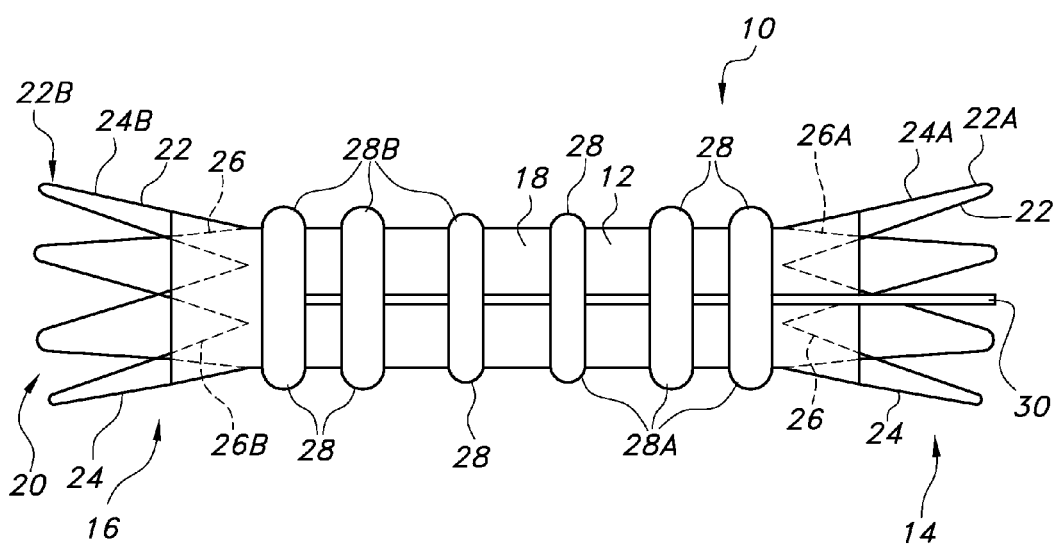
FIG. 1 is an elevational view of a graft assembly useful for treating, e.g., thoracic aortic aneurysms according to the present invention.

Embodiments of the invention are directed generally to methods and devices for treatment of fluid flow vessels with the body of a patient. Treatment of blood vessels is specifically indicated for some embodiments, and, more specifically, treatment of aneurysms, such as, but not limited to, thoracic aortic aneurysms and abdominal aortic aneurysms. The present invention provides various graft assemblies for treatment of blood vessels, including modular graft assemblies, bifurcated graft assemblies, stent-graft assemblies, and combinations thereof.

Modular graft assemblies of the present invention may include a main graft assembly having a network of inflatable channels and a graft. One end the graft assembly may include a graft or stent-graft extension, disposed at, for example, a distal end of the assembly. The graft assembly may be bifurcated or non-bifurcated. The graft assembly may be formed from a supple graft material, such as ePTFE, having a main fluid flow lumen therein. The graft assembly may include porous PTFE which has no discernable node and fibril structure. The bifurcated graft assembly may also include an ipsilateral leg with an ipsilateral fluid flow lumen in communication with the main fluid flow lumen, a contralateral leg with a contralateral fluid flow lumen in communication with the main fluid flow lumen, and a network of inflatable channels disposed on the main graft member. For some embodiments, the main graft member may have an axial length of about 5 cm to about 10 cm; more specifically, about 6 cm to about 8 cm, in order to span an aneurysm of a patient's aorta without engaging the patient's iliac arteries directly with the legs of the main graft member.

The inflatable channels of the network of inflatable channels may be disposed on any portion of the graft assembly including the main body portion, as well as the ipsilateral and contralateral legs. The network of inflatable channels may be configured to accept a hardenable fill material to provide structural rigidity to the main graft member when the network of inflatable channels are in an inflated state and the inflation material has been cured or hardened. Radiopaque inflation material may be used to facilitate monitoring of the fill process and subsequent engagement of graft or stent-graft extensions. The network of inflatable channels may also include at least one inflatable cuff disposed on a proximal portion of the main graft member which is configured to seal against an inside surface of a patient's vessel, such as the aorta. The network of inflatable channels may include at least one longitudinal fill channel in communication with channels at the proximal and distal ends of the device. Further, the network of inflatable channels may include a longitudinal channel in communication with circumferential channels at one end of the device.

A proximal anchor member may be disposed at a proximal end of the main graft member and secured to the main graft member. The proximal anchor member has a self-expanding proximal stent portion secured to a self-expanding distal stent portion with struts. Some embodiments of the struts may have a cross sectional area that is substantially the same as or greater than a cross sectional area of proximal stent portions or distal stent portions adjacent the strut. Such a configuration may be useful in avoiding points of concentrated stress in the proximal anchor member or struts which couple components thereof. For some embodiments, the proximal stent of the proximal anchor member further includes a plurality of barbs having sharp tissue engaging tips that are configured to extend in a radial outward direction in a deployed expanded state. For some embodiments, the proximal anchor member includes a 4 crown proximal stent portion and an 8 crown distal stent portion which may be made from a superelastic alloy such as superelastic nitinol (NiTi) alloy.

For a non-bifurcated graft assembly, at least one graft or stent-graft extension having a fluid flow lumen disposed therein may be deployed with the fluid flow lumen of the extension sealed to and in fluid communication with the fluid flow lumen of the main graft member. The extension may be disposed at the distal end of the main graft member. For a bifurcated graft assembly, at least one ipsilateral extension having a fluid flow lumen disposed therein may be deployed with the fluid flow lumen of the extension sealed to and in fluid communication with the fluid flow lumen of the ipsilateral leg of the main graft member. In addition, at least one contralateral extension having a fluid flow lumen disposed therein may be deployed with the fluid flow lumen of the extension sealed to and in fluid communication with the fluid flow lumen of the contralateral leg of the main graft member. For some embodiments, the extensions may include an interposed self-expanding stent disposed between at least one outer layer and at least one inner layer of supple layers of graft material. The interposed stent disposed between the outer layer and inner layer of graft material may be formed from an elongate resilient element helically wound with a plurality of longitudinally spaced turns into an open tubular configuration. In some embodiments, the interposed stent may have a winding, undulating configuration from the proximal end to the distal end. For some embodiments, the interposed stent is may include a superelastic alloy such as superelastic NiTi alloy. In addition, the graft material of each extension may further include at least one axial zone of low permeability for some embodiments.

For some embodiments, an outside surface of the extension may be sealed to an inside surface of the main graft or a leg of the main graft when the extension is in a deployed state. For some embodiments, the axial length of the ipsilateral and contralateral legs may be sufficient to provide adequate surface area contact with outer surfaces of extensions to provide sufficient friction to hold the extensions in place. For some embodiments, the ipsilateral and contralateral legs may have an axial length of at least about 2 cm. For some embodiments, the ipsilateral and contralateral legs may have an axial length of about 2 cm to about 6 cm; more specifically, about 3 cm to about 5 cm.

Figure 2:
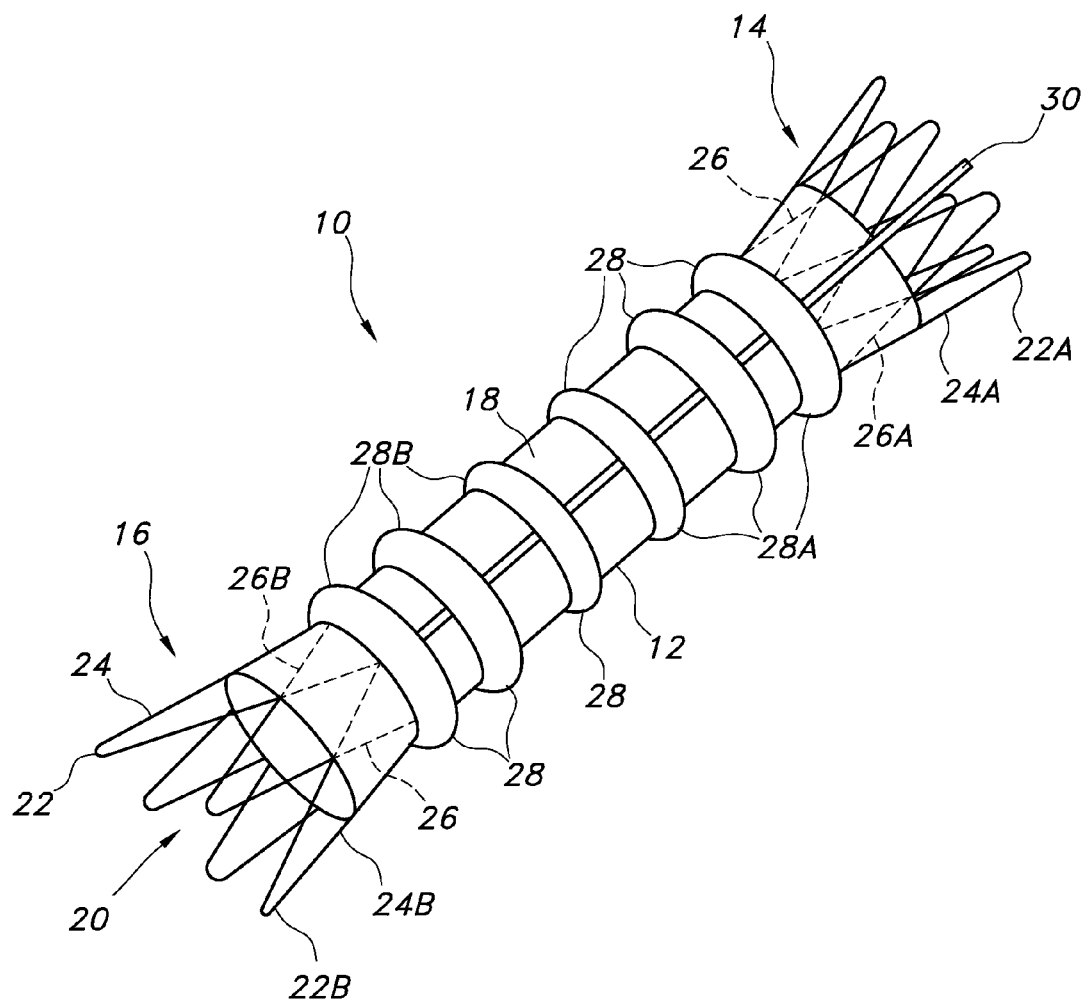
FIG. 2 is a perspective view of the graft assembly of FIG. 1.

FIGS. 1 and 2 depict a graft assembly 10 for the treatment of an aneurysm, such as, but not limited to, a thoracic aortic aneurysm. FIGS. 1 and 2 depict a graft assembly 10 that is non-bifurcated, but it will be understood that the assembly may include a bifurcated portion. As depicted in FIGS. 1 and 2, the graft assembly 10 includes a main graft member 12 disposed between a proximal open end 14 and an opposed open distal end 16. The main graft 12 has a wall portion 18 that bounds a main fluid flow lumen 20 disposed therein and between the opposed open ends 14, 16. The graft wall portion 18 may be made from any biocompatible, durable material, including, for example, polytetrafluoroethylene ("PTFE"), polyethylene terephthalate (PET"), for example DACRON, and the like. Unless otherwise specifically stated, the term "PTFE" as used herein includes PTFE, porous PTFE and ePTFE, any of which may be impermeable, semi-permeable, or permeable. Furthermore, the graft assembly 10 and any portions thereof including the main body and extensions described herein may include all PTFE, all ePTFE, or a combination thereof. In one particular embodiment, the graft wall portion 18 includes a porous PTFE material having no discernable node and fibril structure. Methods of formation of such materials include those methods described in U.S. Patent Application Publication No. 2006/0233990, which is incorporated by reference in its entirety herein.

With regard to graft embodiments discussed herein, such as graft assembly 10, and components thereof, the term "proximal" refers to a location towards a patient's heart and the term "distal" refers to a location away from the patient's heart. With regard to delivery system catheters and components thereof discussed herein, the term "distal" refers to a location that is disposed away from an operator who is using the catheter and the term "proximal" refers to a location towards the operator.

Figure 3:
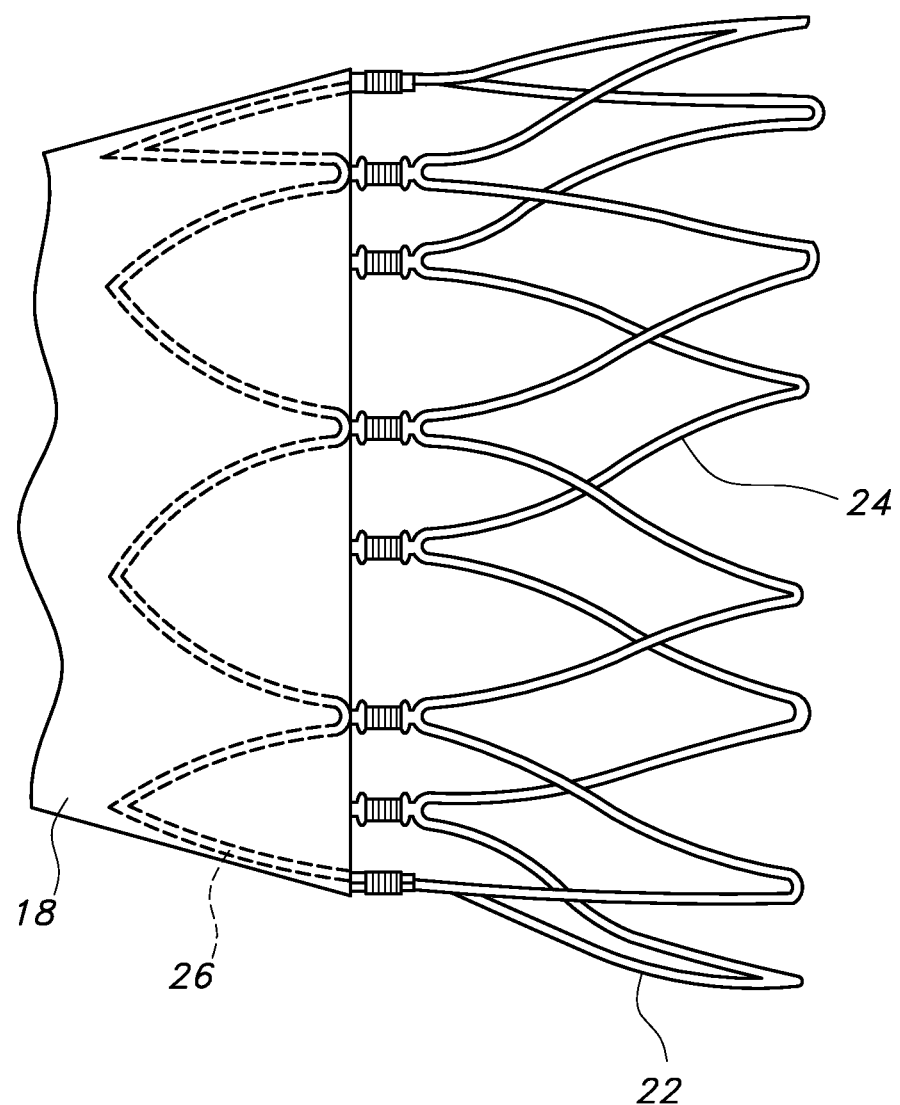
FIG. 3 depicts a close up view of a proximal anchor member and connector ring.

The graft assembly 10 may include a proximal anchor member 22A, which may be disposed at a proximal end 14 of the main graft 12. One representative anchor system may include one as depicted in FIG. 3. The anchor member 22 includes a proximal stent 24, which may be self-expanding or may be balloon-expandable, that is formed from an elongate element having a generally serpentine shape with a number of crowns or apices at either end. As depicted in FIG. 2, six crowns or apices are shown for stent 24A. The number of crowns or apices is not limiting and any suitable number may be used. As depicted in FIG. 3, eight crowns or apices may be used. A distal and/or proximal end of the stent 24 may be mechanically coupled to a connector ring 26 which is embedded in graft material, either at the proximal end 14 of the main graft 12 or the distal end 16 of the main graft 12, or directly coupled to perforations in the proximal or distal edge region of the main graft. Embodiments of the connector ring 26 may be generally circular in shape have regular undulations about the circumference that may be substantially sinusoidal in shape. As depicted in FIGS. 1 and 2, the proximal end 14 of the graft assembly 10 may include a proximal anchor member 22A. The proximal anchor member 22A may similarly include a proximal self-expanding stent 24A, which may be mechanically coupled to a proximal connector ring 26A. In addition, the assembly 10 may include a similar configuration at the distal end 16. The distal end 16 of the graft assembly 10 may include a distal anchor member 22B. The distal anchor member 22B may similarly include a distal self-expanding stent 24B, which may be mechanically coupled to a connector ring 26B. It is understood that the graft assembly 10 may include a proximal anchor member 22A only, a proximal anchor member 22A and a distal anchor member 22B, or neither of a proximal anchor member 22A or a distal anchor member 22B. U.S. Pat. No. 7,147,660, which is incorporated by reference herein, also includes anchor member embodiments that may be used for embodiments discussed herein.

The graft assembly 10 is not limited to the use of connector rings for securing anchor members to the graft portions of the graft assembly 10. Other securing techniques and securing members, such as those disclosed in U.S. applications Ser. No. 13/803,033 to Michael V. Chobotov et al., filed Mar. 14, 2013, entitled "Low Profile Stent Graft And Delivery System"; and Ser. No. 13/803,037 to Jenine S. Vinluan et al., filed Mar. 14, 2013, entitled "Low Profile Stent Graft And Delivery System"; the entirety of each of which is incorporated herein by reference, may suitably be used.

Anchor member 22 may be configured as a self-expanding anchor member having an undulating pattern and may be made from stainless steel, nickel titanium alloy or any other suitable material. The anchor member 22 may be configured to be balloon expandable or self-expanding in an outward radial direction from a radially compressed state. The proximal anchor member 22 and its components may have the same or similar features, dimensions or materials to those of the stents described in U.S. Pat. No. 7,147,660, the content of which is hereby incorporated by reference in its entirety.

A network of inflatable elements or channels (generally depicted as reference numeral 28) is disposed on the graft body 12. The graft assembly 10 may include at least one proximal circumferential inflatable channel 28A and at least one distal circumferential inflatable channel 28B. The inflatable channels 28 may extend around the entire circumference of the graft body 12 or may only extend partially around the circumference of the graft body 12. The at least one proximal circumferential inflatable channel 28A and the at least one distal circumferential inflatable channel 28B may be in communication with each other via a longitudinal inflatable fill channel 30. The longitudinal inflatable fill channel 30 is a tubular structure which is designed to allow communication between the interior of the inflatable channels 28A, 28B. The inflatable channels 28A, 28B may be inflated under pressure with an inflation material (not shown) through a longitudinal inflatable fill channel 30 that has a lumen disposed therein in fluid communication with the network of inflatable channels 28. The inflation material may be retained within the network of inflatable channels 28 by a one way-valve (not shown), disposed within the lumen of the longitudinal inflatable fill channel 30. The network of inflatable channels 28 may optionally be filled with a hardenable material that may be configured to harden, cure or otherwise increase in viscosity or become more rigid after being injected into the channels. Hardenable inflation materials such as gels, liquids or other flowable materials that are curable to a more solid or substantially hardened state may be used to provide mechanical support to the graft body 12 by virtue of the mechanical properties of the hardened material disposed within the channels 28. The network of inflatable channels 28 may also provide structural support to the graft body 12 when in an inflated state due to the stiffness of the channels created by the increased interior pressure within the channels even if a non-hardenable inflation material, such as saline or the like, is used so long as an increased interior pressure can be maintained. Such an increase in stiffness or rigidity may be useful for a variety of purposes. For example, during deployment, inflation of the network of inflatable channels 28 may urge the graft body 12 including the main flow channel and legs thereof to conform to a generally cylindrical configuration having open flow lumens which may be useful when attempting to locate and navigate the flow lumens of the graft assembly 10 with a delivery catheter, guidewire or the like. Such location and navigation of the flow lumens of the graft assembly 10 and portions thereof may also be facilitated by the use of radiopaque inflation materials that provide enhanced visualization under fluoroscopic imaging.

The network of inflatable channels 28 may include one or more circumferential channels disposed completely or partially about the graft body 12 as well as longitudinal or helical channels that may provide support as well as a conduit in communication with the circumferential channels 28 that may be used for filling the network of inflatable channels 28 with inflation material. Some embodiments may also employ radiopaque inflation material to facilitate monitoring of the fill process and subsequent engagement of graft/stent-graft extensions (when used). The network of inflatable channels 28 may also include one or more one or more enlarged circumferential channels in the form of inflatable cuffs. The inflatable cuff (or cuffs) is disposed towards the end of the graft body 12, such as at the proximal end 14 or distal end 16. One example of a proximal inflatable cuff is depicted in FIG. 2 as the circumferential inflatable channel 28A. An inflatable cuff or cuffs disposed at the ends of the body 12 may be configured to seal to an inside surface of a patient's vessel such as a patient's abdominal aorta. An inflatable cuff may be disposed on a portion of the main graft 12 distal of the proximal anchor member 22A and has an outer surface that extends radially from a nominal outer surface of the main graft 12. The inflatable cuff may be configured to expand radially beyond a nominal outer surface of the main graft 12 and provide a seal against an inside surface of a body lumen when the inflatable cuff is inflated with an inflation material to an expanded state. The axial separation of the proximal anchor member 22A and proximal inflatable cuff 28A allows for spatial separation of the primary anchoring mechanism and at least part of the sealing function which may allow the graft to be restrained or otherwise compressed to a smaller outer profile for deployment from a delivery catheter. An interior cavity of any inflatable channels 28 (including one or more inflatable cuffs) is in fluid communication with the interior cavity of the remaining network of inflatable channels 28 and may have a transverse dimension or inner diameter of about 0.040 inch to about 0.250 inch.

Some embodiments of main graft member 12 may include about 1 to about 8 circumferential inflatable channels disposed about the graft body 12. Some embodiments of the graft body 12 may include about 1 to about 4 longitudinal (or axial) inflatable fill channels 30 that may serve to connect the circumferential inflatable channels 28. Some embodiments of the circumferential channels 28 may extend a full circumference of the graft section upon which they are disposed, or they may extend only partially around the graft section upon which they are disposed. For the graft body embodiment 12 shown in FIGS. 1 and 2, the network of inflatable channels 28 includes an inflatable cuff (28A) disposed adjacent the proximal end 14 of the main body portion of the graft body 12. A longitudinal or axial channel extends substantially along the graft body 12 in fluid communication with the circumferential channels 28 and proximal inflatable cuff 28A at the proximal end of the graft body 12. The longitudinal inflatable channel 32 extends between and is in fluid communication with three of the distal inflatable channels 28B. As the inflation material is disposed through the longitudinal fill channel 30, each of the inflatable channels 28 (including proximal inflatable cuff 28A and distal inflatable channels 28B) are filled with inflation material. In addition, the longitudinal inflatable channel 32 is filled with inflation material, resulting in a rigid and strong graft assembly 10.

Some of the inflatable channels 28 of the graft assembly 10 discussed herein may be disposed circumferentially and axially. Alternatively, such inflatable channels 28 may be disposed in spiral, helical, or other configurations. Examples of channel configurations suitable for embodiments of the present invention are described further in U.S. Pat. No. 7,150,758, the entirety of which is incorporated herein by reference. All inflatable channel embodiments described herein as circumferential, may alternatively take on any of the aforementioned alternative configurations. Other modular graft embodiments are discussed in U.S. Patent Application Publication No. 2006/0224232, by Chobotov et al. titled "Hybrid Modular Endovascular Graft", which is hereby incorporated by reference herein in its entirety.

The network of inflatable channels 28, including an inflatable cuff and longitudinal inflatable channel 32, may be filled during deployment of the graft with any suitable inflation material. As discussed above, the inflation material may be used to provide outward pressure or a rigid structure from within the network of inflatable channels 28. Biocompatible gases, liquids, gels or the like may be used, including curable polymeric materials or gels, such as the polymeric biomaterials described in U.S. Pat. No. 7,744,912 and entitled "Biomaterials Formed by Nucleophilic Addition Reaction to Conjugated Unsaturated Groups" to Hubbell et al.; U.S. Pat. No. 6,958,212 and entitled "Conjugate Addition Reactions for Controlled Delivery of Pharmaceutically Active Compounds" to Hubbell et al.; and further discussed in U.S. Pat. No. 7,147,660 and entitled "Advanced Endovascular Graft" to Chobotov, et al., each of which is incorporated by reference herein in its entirety. Some embodiments may use inflation materials formed from glycidyl ether and amine materials, as discussed in U.S. Patent Application Publication No. 2006/0222596 and entitled "Non-Degradable, Low-Swelling, Water Soluble Radiopaque Hydrogel Polymer" to Askari and Whirley, the contents of which are incorporated herein by reference. Some inflation material embodiments may include an in situ formed hydrogel polymer having a first amount of diamine and a second amount of polyglycidyl ether wherein each of the amounts are present in a mammal or in a medical device, such as an inflatable graft, located in a mammal in an amount to produce an in situ formed hydrogel polymer that is biocompatible and has a cure time after mixing of about 10 seconds to about 30 minutes and wherein the volume of said hydrogel polymer swells less than 30 percent after curing and hydration. Some embodiments of the inflation material may include radiopaque material such as sodium iodide, potassium iodide, barium sulfate, Visipaque 320, Hypaque, Omnipaque 350, Hexabrix and the like. For some inflation material embodiments, the polyglycidyl ether may be selected from trimethylolpropane triglycidyl ether, sorbitol polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, polyethylene glycol diglycidyl ether, resorcinol diglycidyl ether, glycidyl ester ether of p-hydroxy benzoic acid, neopentyl glycol diglycidyl ether, 1,6-hexanediol diglycidyl ether, bisphenol A $(PO)_2$ diglycidyl ether, hydroquinone diglycidyl ether, bisphenol S diglycidyl ether, terephthalic acid diglycidyl ester, and mixtures thereof. For some inflation material embodiments, the diamine may be selected from (poly)alkylene glycol having amino or alkylamino termini selected from the group consisting of polyethylene glycol (400) diamine, di-(3-aminopropyl) diethylene glycol r, polyoxypropylenediamine, polyetherdiamine, polyoxyethylenediamine, triethyleneglycol diamine and mixtures thereof. For some embodiments, the diamine may be hydrophilic and the polyglycidyl ether may be hydrophilic prior to curing. For some embodiments, the diamine may be hydrophilic and the polyglycidyl ether is hydrophobic prior to curing. For some embodiments, the diamine may be hydrophobic and the polyglycidyl ether may be hydrophilic prior to curing.

Other inflation materials that may be used for some embodiments include polyethylene oxide materials and neopentyl glycol diacrylate materials which are discussed in U.S. Pat. Nos. 6,610,035 and 6,176,849, which are incorporated by reference herein in their entirety. U.S. Pat. No. 7,147,660, the contents of which are incorporated herein by reference, also includes inflation material embodiments that may be used for embodiments discussed herein.

Figure 4:
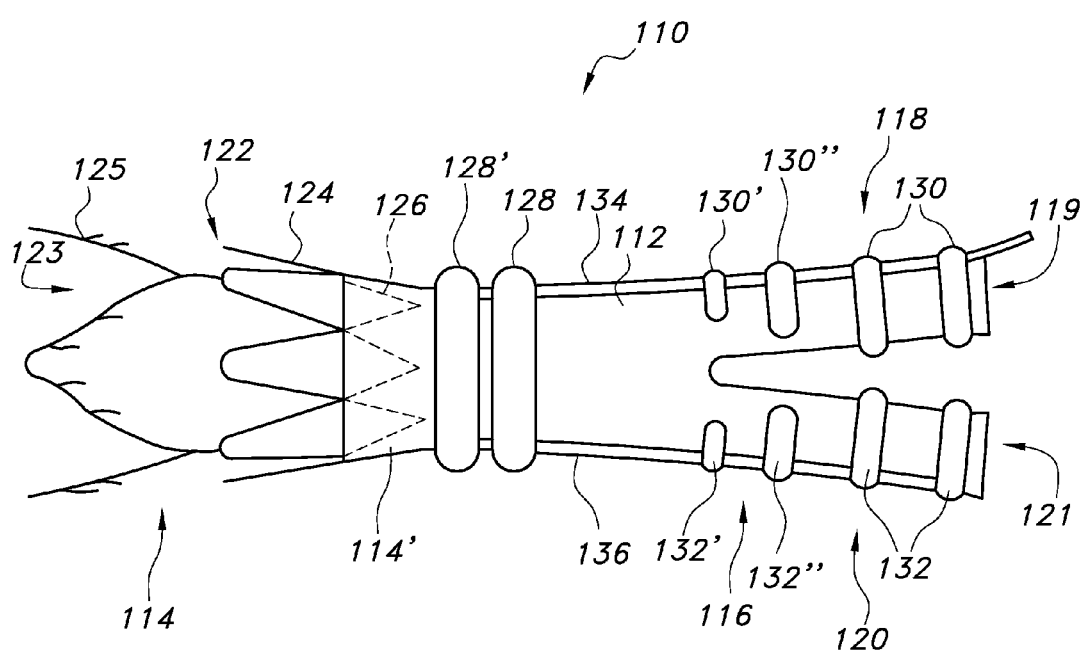
FIG. 4 is an elevational view of a bifurcated graft assembly useful for treating, e.g., abdominal aortic aneurysms according to the present invention.
Figure 5:
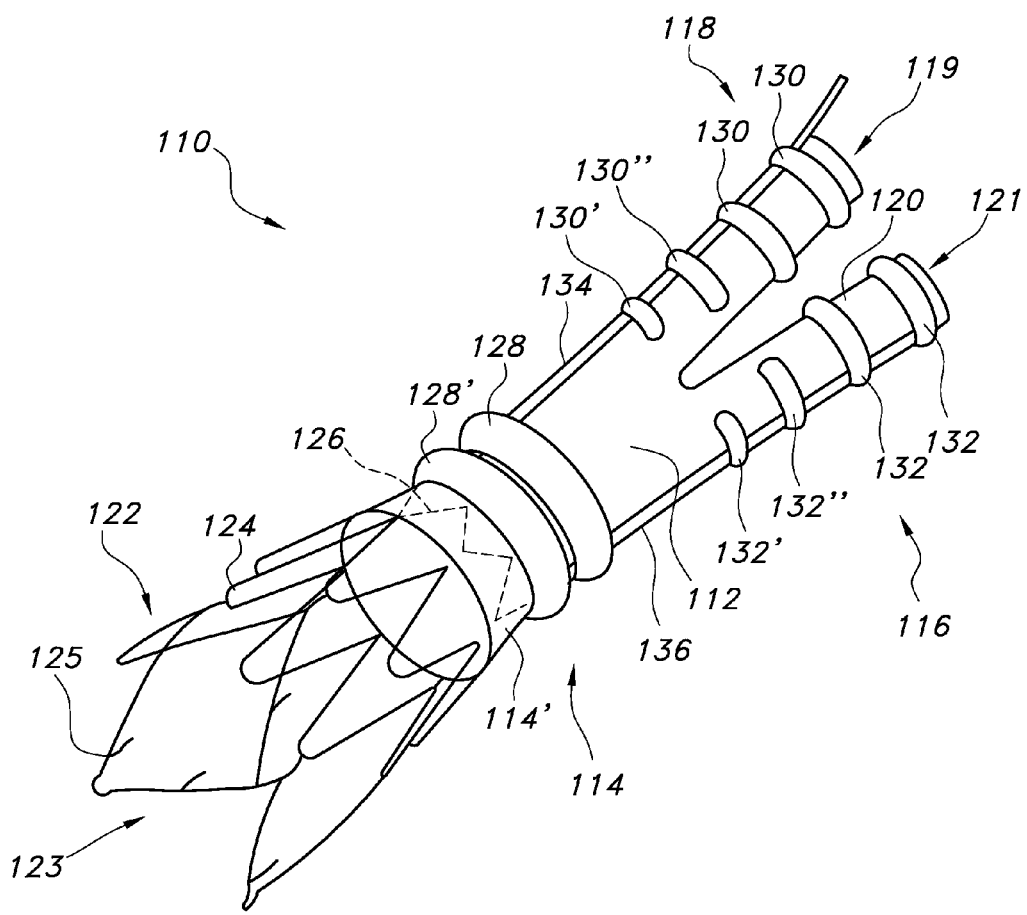
FIG. 5 is a perspective view of the graft assembly of FIG. 4.

FIGS. 4 and 5 show a bifurcated embodiment of a graft assembly 110 for treatment of an abdominal aortic aneurysm. The graft assembly 110 includes a bifurcated main graft member 112, having a proximal end 114 and distal end 116. At the distal end 116, the assembly 110 includes a bifurcated portion, including a first branched leg 118 (having a first leg lumen 119) and a second branched leg 120 (having a second leg lumen 121). In some embodiments, the first branched leg 118 may be referred to as an "ipsilateral leg" 118, and the second branched leg 120 may be referred to as a "contralateral leg" 120. The main graft 112 includes a tubular inner main fluid flow lumen 123 disposed therein. The lumen 123 extends from the proximal end 114 of the graft body 112 to the distal bifurcated region 116. The proximal end 114 includes a proximal anchor member 122, including a proximal stent 124 and proximal connector ring 126, as described above.

The proximal end 114 of the main body portion 112 includes at least one inflatable channel 128. The inflatable channel 128 located closest to the proximal end 114 may be considered an inflatable cuff (designated 128'). The first branched leg 118 includes at least one first branched circumferential inflatable channel 130, and the second branched leg 120 includes at least one second branched circumferential inflatable channel 132. The first branched leg 118 may include at least two first branched circumferential inflatable channels 130, and the second branched leg 118 includes at least two second branched circumferential inflatable channels 132. As explained above, the circumferential inflatable channels (including 128, 130, and 132) may extend the entire circumference of the graft body 112, first branched leg 118 or second branched leg 120, respectively, or may extend only a portion of the circumference. As depicted in FIGS. 4 and 5, the first branched circumferential inflatable channels 130 disposed furthest away from the proximal end 114 may extend the entire circumference of the first branched leg 118, while the first branched circumferential inflatable channels 130 disposed closest to the proximal end 114 may extend only a portion of the circumference of the first branched leg 118. A similar arrangement is desired for the second branched leg 120 and the second circumferential inflatable channels 132.

The first branched leg 118 of the main graft 112 has a first branched leg inflatable fill channel 134, which is in fluid communication with the first branched inflatable channels 130 and the proximal inflatable channel(s) 128. Similarly, the second branched leg 120 includes a second branched leg inflatable fill channel 136, which is in fluid communication with the second branched circumferential inflatable channels 132 and the proximal inflatable channel(s) 128. The main graft 112, first branched leg 118 and second branched leg 120 form a bifurcated "Y" shaped configuration.

The main fluid flow lumen 123 of the main graft 112 generally may have a larger transverse dimension and area than a transverse dimension and area of either of the leg lumens 119 and 121 (shown in FIG. 4) of the first branched leg 118 or second branched leg 120, respectively. A proximal anchor member 122 is disposed at a proximal end 114 of the main graft 112. The proximal anchor member 122 includes a proximal self-expanding stent 124 that is formed from an elongate element having a generally serpentine shape with four crowns or apices at either end, as explained above. A distal end of the proximal stent 124 may be mechanically coupled to a connector ring 126 which is embedded in graft material of the proximal end 114 of the main graft 112, or directly coupled to perforations in the proximal edge region of the main graft 112. Embodiments of the connector ring 126 may be generally circular in shape have regular undulations about the circumference that may be substantially sinusoidal in shape. The proximal stent 124 includes outwardly extending barbs 125, which may be integrally formed with the struts of the stent for some embodiments, having sharp tissue penetrating tips that are configured to penetrate into tissue of an inside surface of a lumen within which the proximal stent 124 is deployed in an expanded state. Although the proximal anchor member 122 is shown as including self-expanding stent 124, similar stents may be used that are configured to be inelastically expanded with outward radial pressure as might be generated by the expansion of an expandable balloon from within stent 124. The connector ring coupled to the proximal stent 124 may also be inelastically expandable.

In a desired embodiment, at least one of the first branched leg 118 and the second branched leg 120 includes at least two inflatable channels. Thus, the first branched leg 118 may include at least two inflatable channels 130, and the second branched leg 120 includes at least two inflatable channels 132. The inflatable channel (130, 132) which is disposed furthest from the proximal end 114 of the graft body 112 may serve as a cuff, as explained above. The inflatable channels 130, 132 may extend around the entire circumference of the leg 118, 120, or may extend only partially around the circumference. In one embodiment, as may best be seen in FIGS. 4 and 5, the inflatable channels 130, 132 which are located closest to the main body portion 112 (labeled 130', 130", 132' and 132") may only extend a portion of the circumference of the leg (118, 120, respectively). Such configuration allows for control while implanting and securing the graft 10 in a patient.

Figure 6:
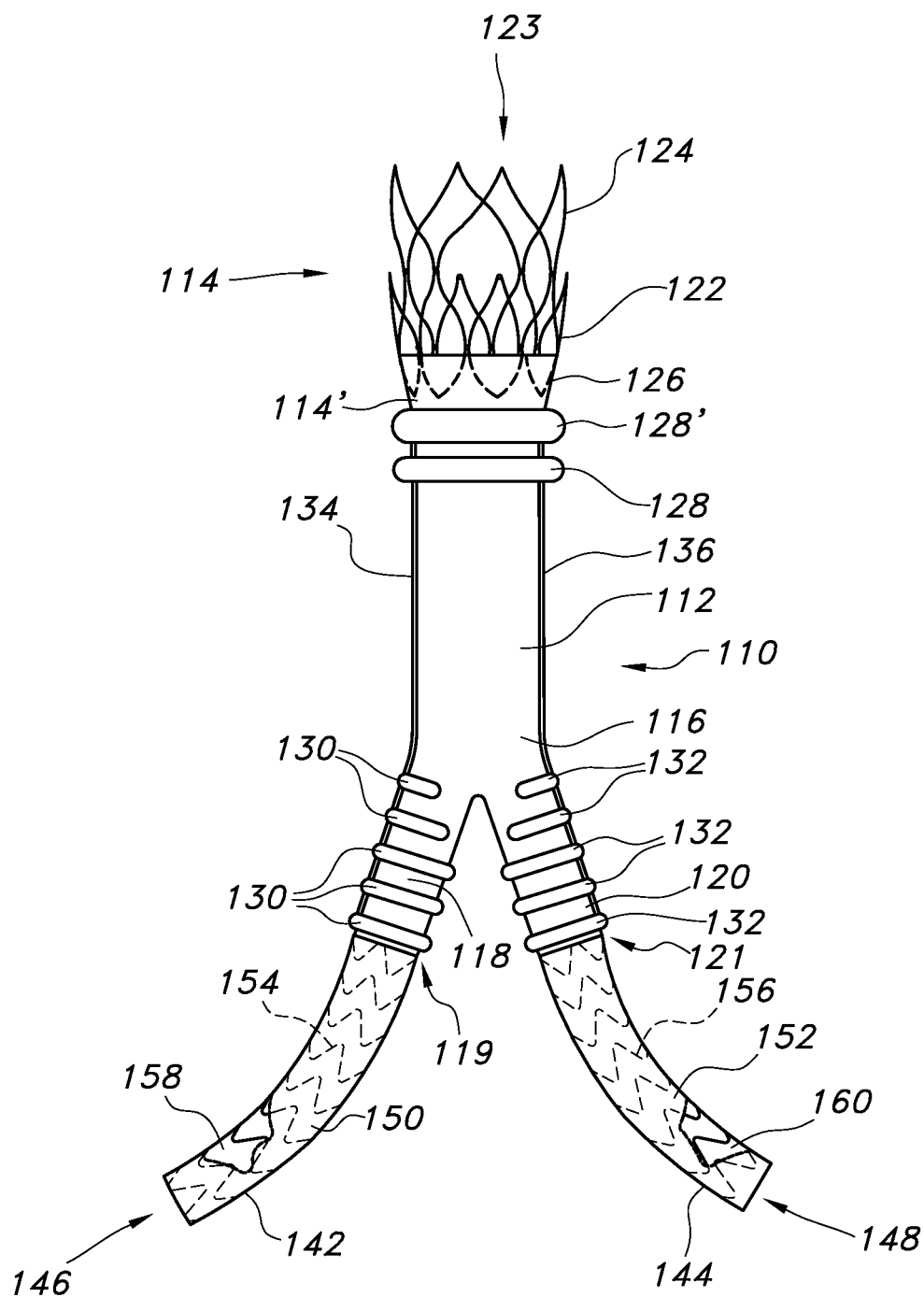
FIG. 6 is an elevational view of a modular bifurcated graft assembly useful for treating, e.g., abdominal aortic aneurysms according to the present invention.

FIG. 6 depicts a modular bifurcated graft assembly 110, which generally includes the bifurcated assembly described above (in FIGS. 4 and 5), but includes optional first and second graft or stent-graft extensions 142, 144. As with the assembly described above, modular bifurcated graft assembly 110 includes a generally tubular main graft body 112, which has a proximal end 114 and distal end 116, with first and second branched legs 118, 120 disposed at the distal end 116. The assembly 110 includes a generally tubular lumen 123 extending through the main graft portion 112 to the bifurcated region and through the lumens (119, 121) of the first and second branched legs 118, 120. The proximal end 114 may include an anchoring device 122, a proximal stent 124, and proximal connector ring 126 connecting the main graft body 112 with the proximal stent 124. The proximal end 114 of the main graft body portion 112 may include one or more proximal circumferential inflatable channel(s) 128, 128'. As with above, the proximal circumferential inflatable channel 128 disposed closest to the proximal end 114 may be considered an inflatable cuff.

Each of the first and second branched legs 118, 120 includes a series of circumferential inflatable channels (first circumferential inflatable channels 130 and second circumferential inflatable channels 132). Any number of circumferential inflatable channels (130, 132) may be used and, as explained above, individual circumferential inflatable channels (130, 132) may extend either the entire circumference of their respective leg (118, 120) or only partially around the circumference. In a desirable embodiment, each leg (118, 120) includes at least two circumferential inflatable channels (130, 132), respectively. It may be desirable to include a first inflatable fill channel 134, which extends along the first branched leg 118 to the proximal end 114 of main graft body 112, and which is in fluid communication with each of the first circumferential inflatable channel(s) 130 and proximal inflatable channel(s) 128. Similarly, it may be desirable to include a second inflatable fill channel 136, which extends along the second branched leg 120 to the proximal end 114 of main graft body 112, and which is in fluid communication with each of the second circumferential inflatable channel(s) 132 and proximal inflatable channel(s) 128'.

Modular bifurcated graft assembly 110 may include one or two graft or stent-graft extensions 142, 144. The first extension 142 has a first fluid flow lumen 146 disposed therein. The first extension 142 has an outer surface which may be sized and configured to be sealed to an inside surface of the first branched leg 118 of the main graft 112 with the inner fluid flow lumen 146 of the first extension 142 in fluid communication with the fluid flow lumen of the first branched leg 118. Typically, an outside surface 150 of the first extension 142 may be sealed to an inside surface of the first branched leg 118 of the main graft 112 when the first extension 142 is in a deployed state. Similarly, the second extension 144 has a fluid flow lumen 148 disposed therein. The second extension 144 has an outer surface 152 which may be sized and configured to be sealed to an inside surface of the second branched leg 120 of the main graft 112 with the second fluid flow lumen 148 in fluid communication with the fluid flow lumen of the second branched leg 120. Typically, an outside surface 152 of the second extension 144 may be sealed to an inside surface of the second branched leg 120 of the main graft 112 when the second extension 144 is in a deployed state.

For some embodiments, the axial length of the first and second branched legs 118 and 120 may be sufficient to provide adequate surface area contact between outer surfaces 150 and 152 of first and second extensions 142 and 144. Additionally, the respective inside surfaces of the first and second branched legs 118 and 120 should provide sufficient friction to the first and second outer surfaces 150, 152 to hold the first and second extensions 142 and 146 in place. Expandable members, such as expandable anchor members and the like, may be used to expand the extensions 142 and 144 against the inside surfaces of the fluid flow lumens of the first and second branched legs 118 and 120. Varying the amount of overlap between the legs and extensions can allow for different effective overall graft lengths to be achieved, thereby accommodating a range of anatomical sizes with fewer distinct main body and extension dimensions than would otherwise be required. For some embodiments, the first and second branched legs 118 and 120 may have an axial length of at least about 1 cm. For some embodiments, the first and second branched legs 118 and 120 may have an axial length of about 2 cm to about 6 cm; more specifically, about 3 cm to about 5 cm.

Some embodiments of main graft member 112 may include about 1 to about 8 circumferential inflatable channels 130,132 disposed about each leg 118, 120 and about 1 to about 8 proximal circumferential channels 128 disposed about a main body portion of the main graft member 112. Some embodiments of the main graft body member 112 may include about 1 to about 4 longitudinal or axial inflatable fill channels 134, 136 that may serve to connect the circumferential inflatable channels (128, 130, 132). Some embodiments of the circumferential channels may extend a full circumference of the graft section upon which they are disposed, or they may extend only partially around the graft section upon which they are disposed. For the main graft member embodiment 112 shown in FIG. 6, the network of proximal inflatable channels 128, 128' includes an inflatable cuff 128' disposed adjacent the proximal end 114 of the main body portion 112 and a circumferential channel 128 disposed just distal of the inflatable cuff 128'. Each leg 118 and 120 of the main graft member 112 includes 3 complete circumferential inflatable channels 130, 132 in axial series. Each leg 118 and 120 of the main graft member 112 also has two partial circumferential inflatable channels 130, 132 disposed proximally of the complete circumferential inflatable channels 130, 132.

For some method embodiments of treating the vasculature of a patient, a modular graft assembly, such as the modular graft assembly embodiments 110 discussed above, may be used. Various methods of delivery systems and delivery of the device into a patient include those described in Applicant's co-pending application, U.S. Patent Application Publication No. 2009/0099649, the contents of which are incorporated by reference in entirety herein. For endovascular methods, access to a patient's vasculature may be achieved by performing an arteriotomy or cut down to the patient's femoral artery or by other common techniques, such as the percutaneous Seldinger technique. For such techniques, a delivery sheath (not shown) may be placed in communication with the interior of the patient's vessel such as the femoral artery with the use of a dilator and guidewire assembly. Once the delivery sheath is positioned, access to the patient's vasculature may be achieved through the delivery sheath which may optionally be sealed by a hemostasis valve or other suitable mechanism. For some procedures, it may be necessary to obtain access via a delivery sheath or other suitable means to both femoral arteries of a patient with the delivery sheaths directed upstream towards the patient's aorta. In some applications a delivery sheath may not be needed and a delivery catheter may be directly inserted into the patient's access vessel by either arteriotomy or percutaneous puncture.

The first and second extensions 142 and 144 may be formed from an inner layer or layers and outer layer or layers of flexible graft material, such as PTFE or ePTFE. In one embodiment, the flexible graft material includes PTFE which is substantially porous but includes no discernable node and fibril structure. The inner and outer layers of graft material may be formed from tubular extrusions, laminated wraps of multiple layers of graft material or materials, and the like. The inner or outer layers of graft material may be permeable, semi-permeable or substantially non-permeable for some embodiments. For some embodiments, the nominal length of the extensions 142 and 144 may be permeable with one or more longitudinal sections, such as a middle longitudinal section, being semi-permeable or non-permeable. Some embodiments of the extensions 142 and 144 may have an overall tapered or flared configuration with a nominal inner lumen that tapers or flares when the extension is in a relaxed expanded state. For embodiments that include laminated wraps of material, the wraps may be carried out circumferentially, helically or in any other suitable configuration.

The first and second leg extensions 142, 144 are desirably stent-graft devices. A first radially expandable stent 154 may be interposed between an outer layer 150 and inner layer 158 of graft material. A second radially expandable stent 156 may be interposed between an outer layer 152 and inner layer 160 of graft material. The interposed stent 154, 156 disposed between the outer layer 150, 152 and inner layer 158, 160, respectively, of graft material may be formed from an elongate resilient element helically wound with a plurality of longitudinally spaced turns into an open tubular configuration. The helically wound stent 154, 156 may be configured to be a self-expanding stent or radially expandable in an inelastic manner actuated by an outward radial force from a device such as an expandable balloon or the like. Some tubular prosthesis embodiments that may be used for extensions 142 and 144 are discussed in U.S. Pat. No. 6,673,103 to Golds et al., titled "Mesh and Stent for Increased Flexibility", which is hereby incorporated by reference in its entirety herein.

The extensions 142 and 144 may optionally include attachment elements disposed on outer surfaces 150, 152 of their respective proximal ends or sections that may be used to couple to corresponding attachment elements disposed on inside surfaces of the respective first branched leg 118 and second branched leg 120 of the main graft 112. Attachment element embodiments that may be used on outside surfaces 150 and 152 of extensions 142 and 144 and inside surfaces of first and second branched legs 118 and 120 of the main graft 112 may include any of the attachment elements in U.S. Patent Application Publication No. 2005/0228484, entitled "Modular Endovascular Graft", by Stephens et al., which is hereby incorporated by reference herein in its entirety. The first graft body section may have a first wall portion and a first attachment element disposed on the first wall portion and the second graft body section may have a second attachment element disposed on a second wall portion of the second graft body section. The second attachment element may be configured to be secured to the first attachment element with respective fluid flow lumens of the first and second graft body sections sealed together. For some embodiments, the first and second attachment elements may be secured together in an overlapped portion of the first and second graft body sections. For some embodiments, the first attachment element may include a plurality of flexible hooks and the second attachment element includes a plurality of flexible loops adjacent each other wherein the flexible hooks are configured to mechanically engage the flexible loops when the first and second attachment elements are pressed together. For some embodiments, the first attachment element includes a plurality of buttons having an enlarged head portion regularly spaced from each other on a surface a first wall portion and a second attachment element includes an expandable mesh having a plurality of apertures configured to allow entry of the enlarged head portion of the buttons while the mesh is in a circumferentially constrained state and to capture the enlarged head portion of the buttons when the mesh is in a circumferentially expanded state. For some embodiments, the first attachment element includes a plurality of pins radially extending from a surface of a first wall portion and the second attachment element includes an expandable mesh having a plurality of apertures configured to allow entry of the pins when the first attachment element is pressed against the second attachment element. For some embodiments the first attachment element may include an inflatable cuff containing curable material and the second attachment element includes an expandable member with barbs configured to extend outwardly into the inflatable cuff and curable material.

Extensions 142 and 144, which may be interchangeable for some embodiments, or any other suitable extension devices or portions of the main graft section 112 may include a variety of suitable configurations. Alternatively, extensions 142, 144 may be useful as a separate endovascular stent-graft, apart from the bifurcated graft assembly 110. For some embodiments, extensions 142 and 144 may include a PTFE covered helical nitinol stent 154, 156 as discussed above with layers of PTFE having a variety of characteristics. Regarding the stent 154, 156, it may be formed from an elongate resilient element which is helically wound with a plurality of longitudinally spaced turns.

Figure 7:
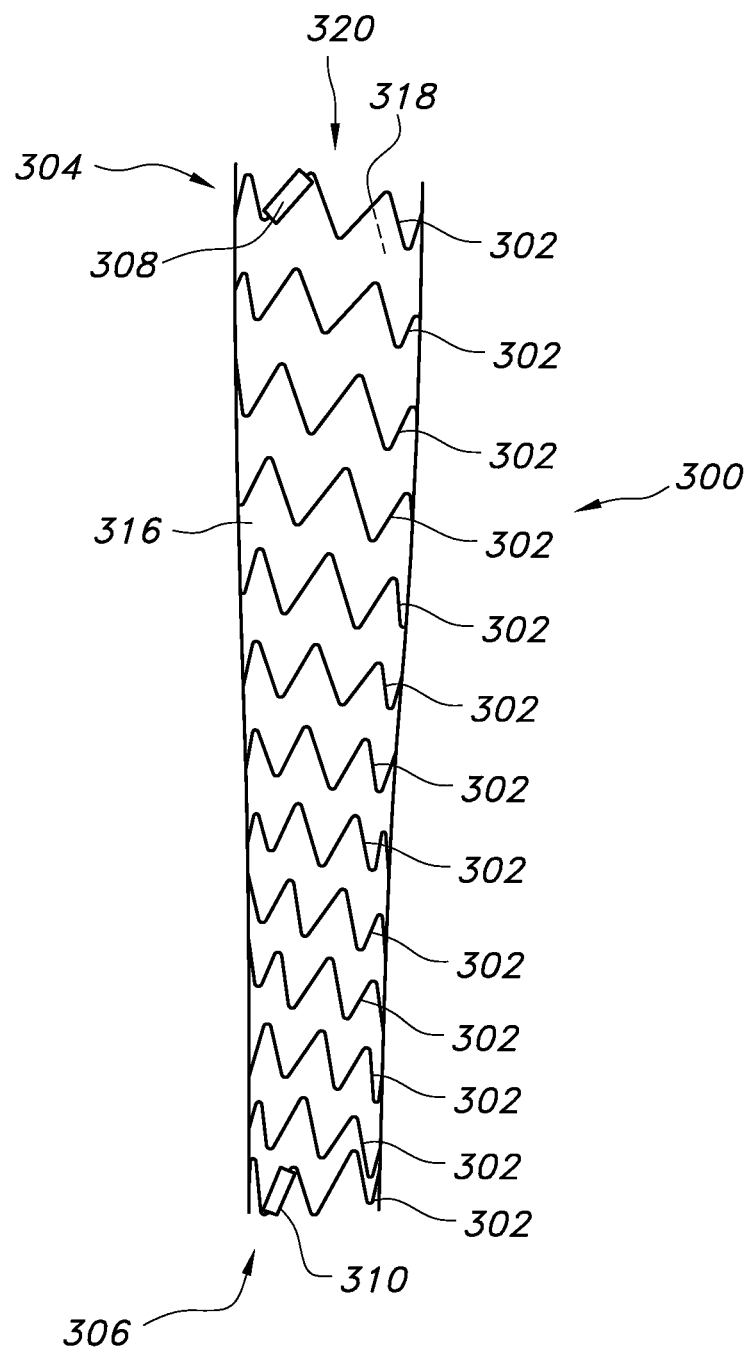
FIG. 7 depicts one embodiment of a stent structure useful in the present invention.
Figure 8:
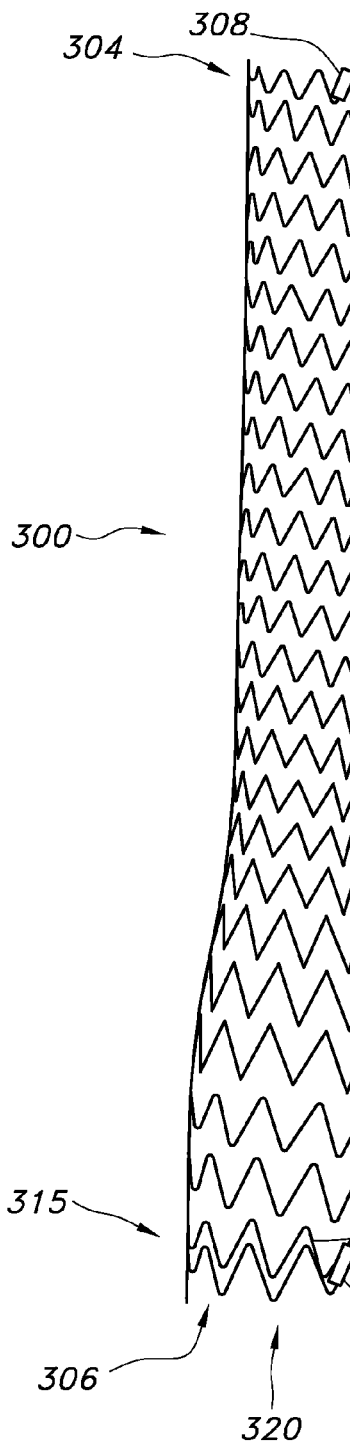
FIGS. 8 and 9 depict additional embodiments of stent structures useful in the present invention.
Figure 9:
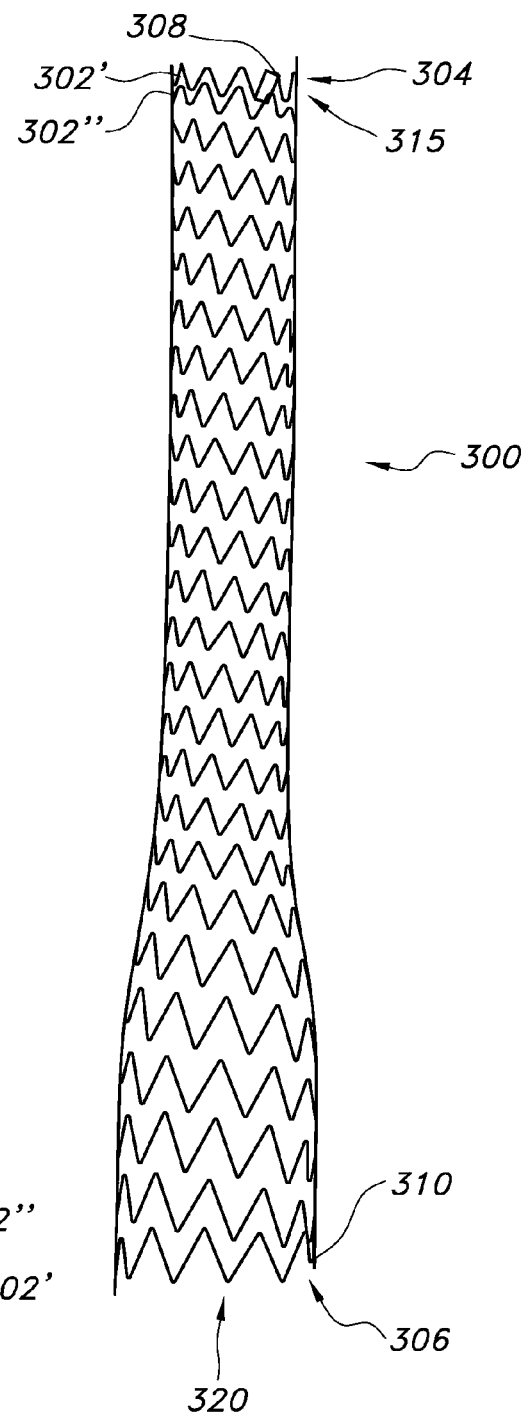

Some stent embodiments may be generally helical in configuration with serpentine or other regularly spaced undulations transverse to the helical path of the elongate stent element as shown in more detail in FIGS. 7 through 9.

As can be seen, a generally tubular stent 300 may be provided. The tubular stent 300 includes a helically-wound, undulating wire forming a series of adjacent helical windings 302, which may be made from the materials described above (including a resilient metal such as nitinol). The ends 304, 306 of the stent 300 may be secured to adjacent ring portions of the stent at distinct areas. For example, a first end may be adjoined via a first securement point 308, and a second end may be joined at a second securement point 310, as shown to avoid exposure of element ends to either PTFE graft material or possible patient tissues. In a preferred embodiment, the securement points 308, 310 are located proximal to the first end 304 and second end 306, respectively, with no other securement points on the stent 300. That is, aside from the helical windings 302 at the first end 304 and second end 306, respectively, adjacent approximate circumferential windings 302 in the stent 300 may be free of interconnecting securement points. Any securement means may be used, including, for example, welding, such as struts and welds. It is desired that the relative stiffness of a stent be greater than the stiffness of the PTFE graft material so as to provide beneficial kink resistance.

The undulating wire may be a continuous element forming a series of helical windings 302 extending from one end 304 of the extension to the other end 306 thereof. The tubular stent 300 thus has an internal lumen 320 extending there through, from the first end 304 to the second end 306. The ends 304, 306 of the elongate element may be secured to adjacent ring members by any suitable means such as adhesive bonding, welding such as laser welding, soldering or the like. For some embodiments, the stent element may have a transverse dimension or diameter of about 0.005 inch to about 0.015 inch. As may be seen in FIGS. 9A and 9B, the stent 300 may be tapered or flared. In addition, if desired, adjacent helical windings 302 may be arranged 315 such that adjacent helical windings 302 at one end (either the first end 304 or second end 306) have an acute angle formation at a portion of the stent 300 proximal to the end of the stent 300. That is, if desired, the helical winding closest to the end (shown as 302') may have an approximately 180° angle with respect to the longitudinal axis, while the helical winding next to this helical winding (shown as 302") has an angle less than 180°. These two helical windings (302' and 302") may be attached at securement points 308, 310.

At least one graft layer may be disposed on the stent 300. In some embodiments, an inner graft layer 318 may be disposed on the interior surface of the helically wound stent 300, forming inner lumen 320. A second graft layer 316 may be disposed on the outer surface of the helically wound stent 300, forming an outside surface. More than one or two layers of graft material may be disposed on the interior or exterior of the helically wound stent 300 as desired. For some embodiments of first or second extensions 142, 144, layers of materials having different properties may be used in combination to achieve a desired clinical performance. For example, some layers of PTFE covering the stent 300 may be permeable, semi-permeable or substantially non-permeable depending on the desired performance and material properties. The layers 316 and 318 may be applied by a variety of methods and have a variety of configurations. For example, some layer embodiments may include extruded tubular structures applied axially over a mandrel or subassembly. Some layer embodiments 316 and 318 may be applied by wrapping layers circumferentially or wrapping tapes or ribbons in an overlapping helical pattern. For some embodiments, the outer layer 316 may be made from or include a semi-permeable or substantially non-permeable PTFE layer and the inner layer 318 may be made of or include a permeable layer of PTFE.

The first and/or second extensions 142, 144 may be made by forming the layers of material 316, 318 together with the helically wound stent 300 over a mandrel, such as a cylindrical mandrel (not shown). Once the innermost layer 316 of the extension 142, 144 has been wrapped about a shaped mandrel, a helical nitinol stent, such as helical stent 300, may be placed over the innermost layered PTFE layer 316 and underlying mandrel. If desired, one or more additional layers 318 of graft material may be wrapped or otherwise added over the exterior of the stent 300. If desired, the outer layer 318 may include low permeability PTFE film or PTFE film having substantially no permeability that does not have the traditional node fibril microstructure. The mandrel may then be covered with a flexible tube such that the layers 316, 318 and stent 300 are sandwiched under pressure and sintered so as to raise the temperature for the PTFE material to undergo a melt transformation in order to lock in its geometry and strength. The flexible tube (a manufacturing aid not shown) is removed from over the device and the resultant extension (142, 144) is removed from the mandrel.

The main graft 112 and graft portions of the first and second extensions 142 and 144 may be made at least partially from polytetrafluoroethylene (PTFE) which may include expanded polytetrafluoroethylene (ePTFE). In particular, main graft 112 and extensions 142 and 144 may include any number of layers of PTFE and/or ePTFE, including from about 2 to about 15 layers, having an uncompressed layered thickness of about 0.003 inch to about 0.015 inch for the supple graft material or materials alone without supporting or ancillary structures such as high strength stents, connector rings or the like. Such graft body sections may also include any alternative high strength, supple biocompatible materials, such as DACRON, suitable for graft applications. Descriptions of various constructions of graft body sections as well as other components of graft assembly 110 that may be used in any suitable combination for any of the embodiments discussed herein may be found in U.S. Pat. No. 7,125,464 to Chobotov, et al., entitled "Method and Apparatus for Manufacturing an Endovascular Graft Section"; U.S. Pat. No. 7,090,693 to Chobotov et al., entitled "Endovascular Graft Joint and Method of Manufacture"; U.S. Pat. No. 7,147,661, entitled "Method and Apparatus for Shape Forming Endovascular Graft Material", to Chobotov et al.; U.S. Pat. No. 7,147,660 to by Chobotov et al., entitled "Advanced Endovascular Graft"; U.S. Patent Application Publication No. U.S. 2006/0233990 to Humphrey et al. entitled "PTFE Layers and Methods of Manufacturing"; and U.S. Patent Application Publication No. 2006/0233991 to Humphrey et al., entitled "PTFE Layers and Methods of Manufacturing", the entirety of each of which is incorporated herein by reference.

Additional details of the above-described graft assemblies, including modular components, may be found in U.S. application Ser. No. 13/803,046 to Sarah Young et al., filed Mar. 14, 2013, entitled "Advanced Kink Resistant Stent Graft"; the entirety of which is incorporated herein by reference.

Figure 10:
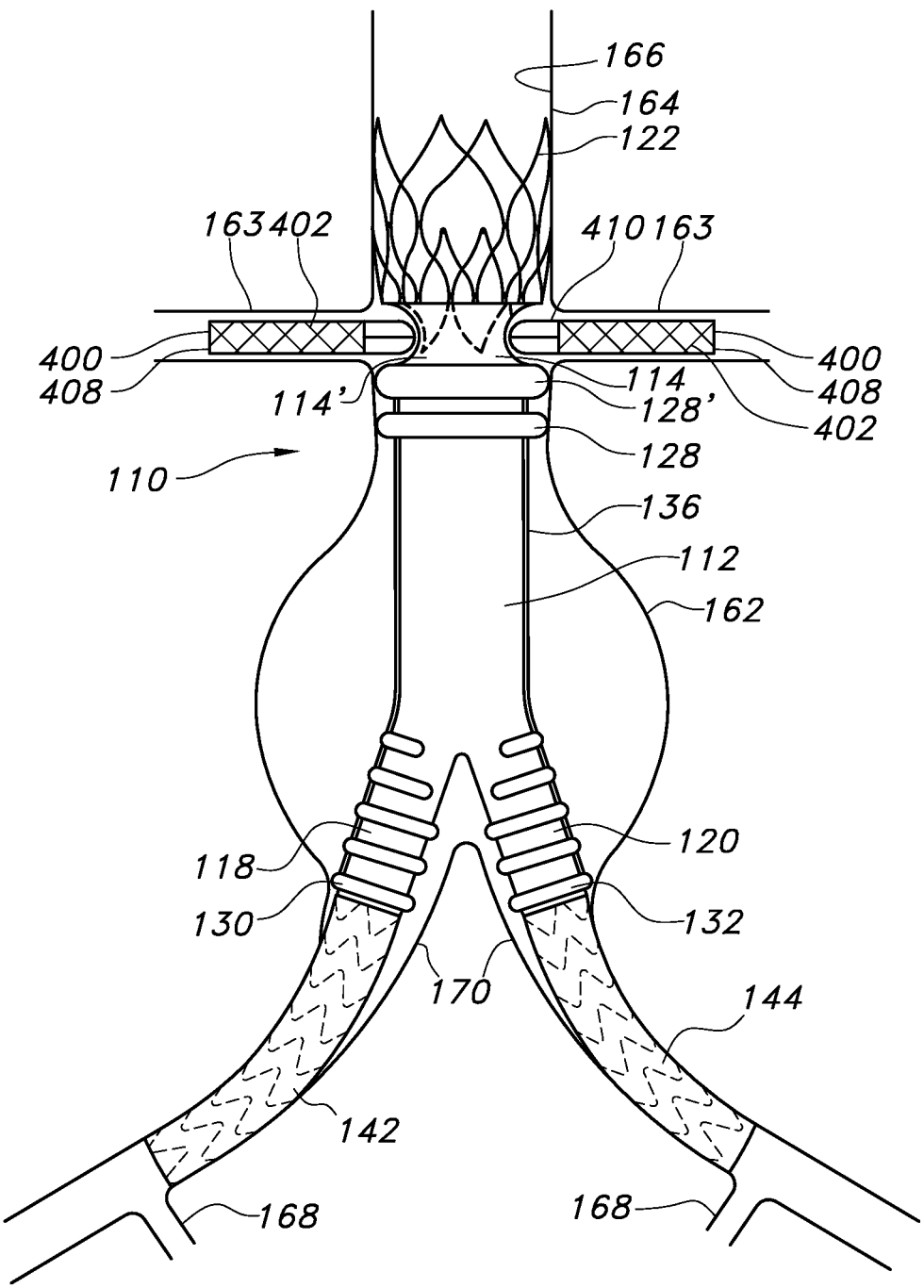
FIG. 10 depicts the modular bifurcated graft assembly of FIG. 6 in an implanted state in conjunction with a renal vent device.

FIG. 10 depicts the assembly of FIG. 6 in a deployed state. As can be seen, in its deployed state, the modular bifurcated graft assembly 110 includes a first and second stent-graft extension 142, 144 disposed in the first and second branched legs 118, 120. The main body portion 112 and first and second branched legs 118, 120 span or substantially span the diseased region of abdominal aorta or aneurysm 162, providing safe passage there through. The proximal end 114 of the main graft body 112 is disposed in the aorta 164 near the renal arteries 163. A portion, including a substantial portion, of the graft collar portion 114' may partially or fully bridge the renal arteries 163. In the embodiment depicted in FIG. 10 the entire anchoring device 122 is disposed beyond the renal arteries 163 while the graft collar portion 114' spans or bridges the renal arteries 163. The proximal circumferential inflatable channel 128' acts as a cuff, holding the assembly 110 in place. The proximal circumferential inflatable channel 128 may further perform these sealing and securing functions. The first and second stent-graft extensions 142, 144 may extend from above the hypogastric arteries 168 and into and/or through the iliac arteries 170.

To allow placement of the assembly 110 such that its sealing ring or proximal circumferential inflatable channel 128' is just distal to the lowest renal artery 163, a separate renal vent device(s) 400 may be used that keeps the graft collar 114' or proximal end 114 of the main graft body 112 from covering the renal artery or arteries 163. The use of renal vent device(s) 400 allow for, among other things, treating larger neck diameters arteries as the aortic sizing location would not be limited by a longitudinal length of the proximal end 114 of the main graft body 112. For example, proximal end 114 of the main graft body 112 often may have a non-limiting length representing about 13 mm plus the internal radius ("IR") of the proximal end 114 of the main graft body 112 (or IR+13 mm). With the use of the renal vent device(s) 400, the proximal end 114 of the main graft body 112 may have a non-limiting length of approximately IR+3 mm or 4 mm. Such lengths are non-limiting, and other lengths for example, from about 1 mm to about 10 mm, from about 1 mm to about 5 mm, from about 1 mm to about 3 mm, and the like, may suitably be used.

While FIG. 10 depicts the placement of endovascular devices, such as the modular bifurcated graft assembly 110 and/or the renal vent devices 400, at or near the renal arteries 163, the present invention is not so limited. More generally, a renal vent device 400 may also be referred to as a branched artery vent device 400' and may be used in any of the branched arteries within the body, typically branched vascular arteries. Furthermore, the renal vent device 400 and/or the branched artery vent device 400' may be used in conjunction with any of the endovascular devices, such as the graft assembly 10, the graft assembly 110, stent or stent-grafts 142, 144, 300, as described herein.

Figure 11:
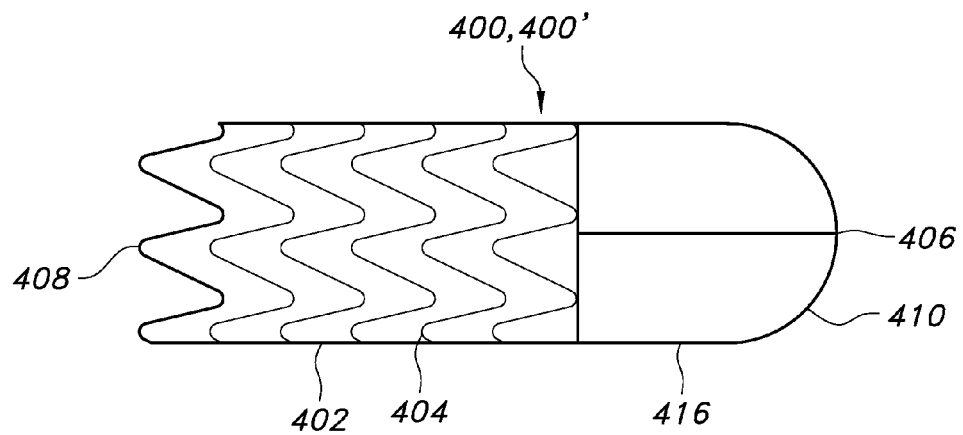
FIGS. 11-13 depict embodiments of a renal vent device.
Figure 12:
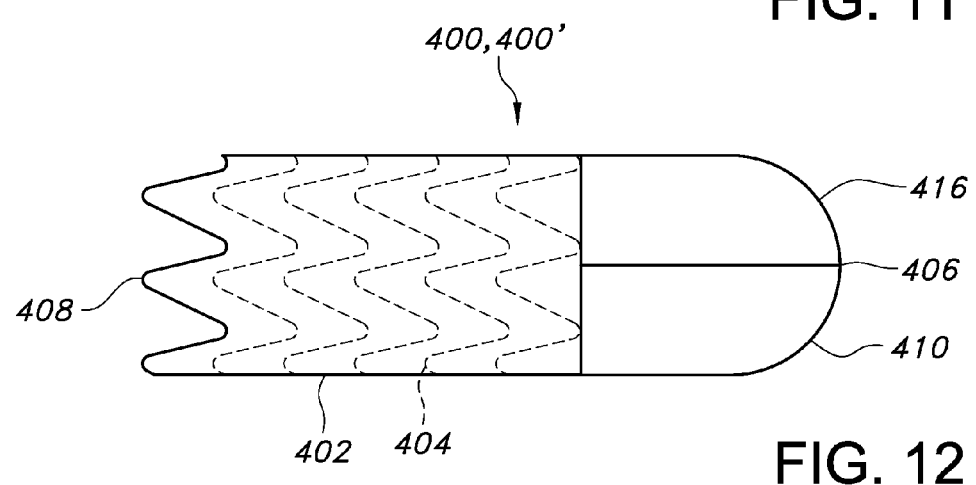
Figure 13:
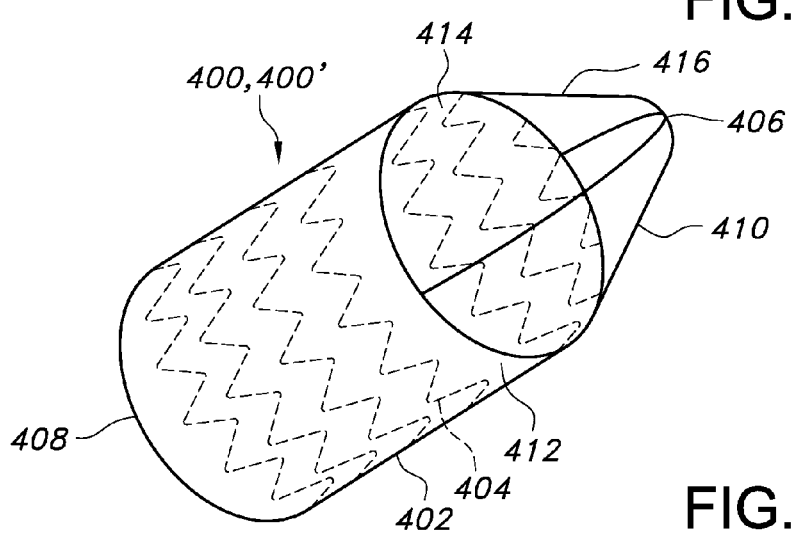

Details of the renal vent device 400 or branched artery vent device 400' are depicted in FIGS. 11-13. The devices 400, 400' may include a main body portion 402 having a stent 404. While the stent 404 is depicted as having similar pitch along its length, the present invention is not so limited. For example, the stent 404 may have a variable pitch to further control radial force and/or crush resistance along its length as may be required. For example, the stent 404 could be more flexible in a middle region with a coarser pitch and/or have more radial strength at one or both of its stent ends by having a finer pitch or tighter winding angle. The main body portion 402 may include an open end 408, which is typically disposed within the renal 163 or branched artery. Opposed the open end 408 is another generally open end 406. The open end 408 includes a stand-off 410 to separate it from the main body portion 402 having the stent 404. As depicted in FIGS. 11-13, the stand-off 410 may be an open interstitial member having elongate members or wires 416 extending from the main body portion 402 to open end 406. The wires 416 at the open end 406 form an atraumatic end configured to keep the graft collar 114' or proximal end 114 of the main graft body 112 from covering the renal artery or arteries 163 by, for example, pushing a portion of the graft collar 114' or proximal end 114 of the main graft body 112 from the main arterial wall. The stand-off 410 may be described as a cage having open interstitial spaces with an atraumatic cage end for engaging and pushing a pushing a portion of the graft collar 114' or proximal end 114 of the main graft body 112 from the main arterial wall. While the stand-off or cage 410 is depicted simply as two curved wires 416 forming an atraumatic open cage end 406, any suitable number of wires and/or configurations may be used. Furthermore, the present invention is not limited to a renal vent device 400, 400' with the open cage end 406. The open cage end 406 may be a non-open-cage end (not shown) in the form of an atraumatic stent end, e.g., a stent end preferably having no sharp members or edges that may potentially cause undesirable harm to body lumens or tissue, such as, but not limited to, the stent ends depicted in FIGS. 7-9. Such a non-open-cage but atraumatic end may be useful where the open stent end of the renal vent device 400, 400' extends above the proximal end 114 of the main graft body 112. The main body portion 402 may include an outer graft layer or layers 412 and/or an inner graft layer or layers 414.

The renal vent device 400 or branched artery vent device 400' may be described as being similar to a conventional stent, only with a blunt, open protruding stand-off 410 which extends, for example, from the ostium of a branched artery about 4 to 6 mm to prevent the graft collar 114' or a portion of the endovascular device present in the main artery from closing off the branched, for example renal, artery. The graft collar 114' near the renal 163 is pushed away from the aortic wall 166, forming a vent for the renal artery 163. This device 400, 400' can be made from bare nitinol (wire wound or laser-cut), or be balloon expandable. Its delivery catheter may be inserted into the renal using femoral access before deployment of the aortic body or main graft member 112, and a pullback deployment may be performed to anchor it into the renal 163. A marker on the device and/or delivery catheter may indicate the depth of insertion required to ensure the extent of protrusion is adequate. The protruding section can be a set of crossing semicircular shaped metal segments joined transversely. The delivery profile can be quite low (for example, 6 to 7 French or less) as a covering of graft material need not be used. Since the attachment ring or proximal connector ring 126 in the graft collar 114' or proximal end 114 of the main graft body 112 may be encapsulated in graft material, such as PTFE, no direct metal-to-metal contact is present, which greatly enhances durability within the human body. Use of such devices 400, 400' is much simpler than fenestrated grafts.

While the renal vent device 400 and/or the branched artery vent device 400' may be used in conjunction with any of the endovascular devices, such as the graft assembly 10, the graft assembly 110, stent or stent-grafts 142, 144, 300, as described herein, the use of the renal vent device 400 and/or the branched artery vent device 400' is more suitably used on graft or stent-graft assemblies that have separate and distinct sealing and anchoring functions. For example, the graft assemblies 10, 110 of the present invention have separate and distinct sealing and anchoring functions by virtue of, for example, the inflatable cuffs 28, 28A, 128, 128' and the proximal anchors 22A, 122; respectively. Such graft assemblies 10, 110 are particularly useful with the renal vent device 400 and/or the branched artery vent device 400' as these devices 400, 400' may be positioned at a graft collar 114' between the sealing function, i.e., inflatable cuffs 28, 28A, 128, 128', and the anchoring function, i.e., proximal anchors 22A, 122, of the graft assemblies 10, 110 where the graft collar 114' or a portion of the graft collar 114' bridges a branched side artery.

Figure 14:
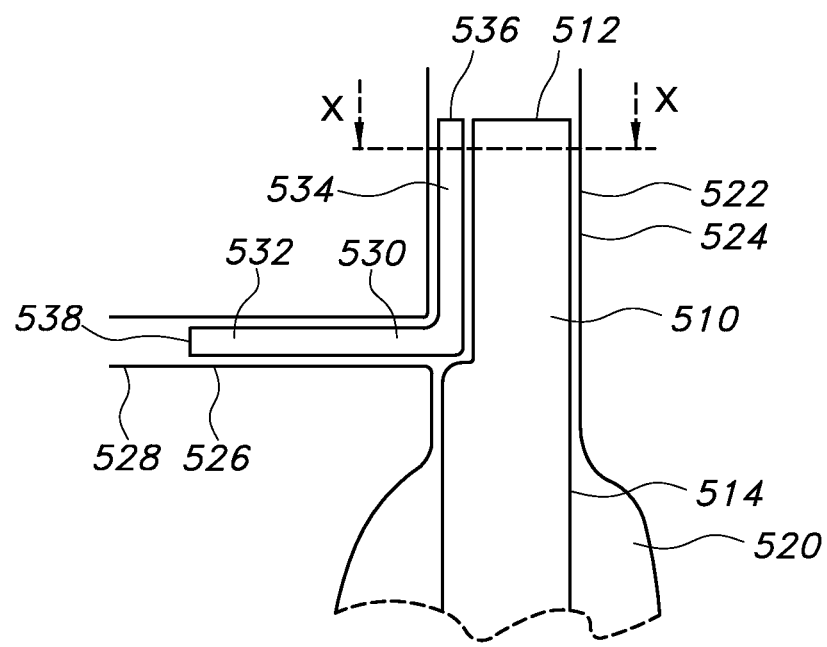
FIG. 14 depicts a main graft and a chimney graft useful for treating branched arteries.

FIG. 14 depicts another embodiment of the present for provide a path of fluid flow to a branched side artery from a main artery where a graft in the main artery bridges, including partially bridging, substantially bridging, totally bridging, and the like, the branched artery. As depicted in FIG. 14, the main artery 522 having an artery wall 524 has a diseased portion, such as an aneurysm 520. A side branched artery 528 is depicted as being proximally disposed to the diseased portion or aneurysm 520. A main graft or stent-graft 510 is positioned within the main artery 522, including at least a portion of the diseased portion 520 or aneurysm 520. A proximal end 512 of the main graft or stent-graft 510 is depicted as completely spanning the side branched artery 528 with a proximal end 512 of the main graft or stent-graft 510 being disposed proximally beyond the side branched artery 528. A chimney graft or stent-graft 530 has a distal portion 532 disposed within the side branched artery 528 and has a proximal portion 534 disposed within the main artery 522. The proximal end of the proximal portion 534 of the chimney graft or stent-graft 530 is disposed at least to about the same extent of the proximal end 512 of the main graft 510 within the main artery 522. Often the proximal end of the proximal portion 534 of the chimney graft or stent-graft 530 is disposed beyond the proximal end 512 of the main graft 510 within the main artery 522. The chimney graft or stent-graft provides fluid communication, for example blood flow, from the main artery 522 to the side branched artery 528 while the main graft or stent-graft 510 provides for fluid communication, for example blood flow, within the main artery. Any of the above described graft assembly 10, graft assembly 110, stent or stent-grafts 142, 144, 300 may suitable be used as the main graft or stent-graft 510. Further, any of the above described graft assembly 10, graft assembly 110, stent or stent-grafts 142, 144, 300 may suitable be used as the chimney graft or stent-graft 530, especially including modifications and/or embodiments described below in conjunction with FIGS. 16-31. Moreover, the chimney stent-graft 530 may include a stent having a similar stent pitch along its length or a variable stent pitch as described above for the stent 404 of the renal vent device 400, 400'.

Figure 15:
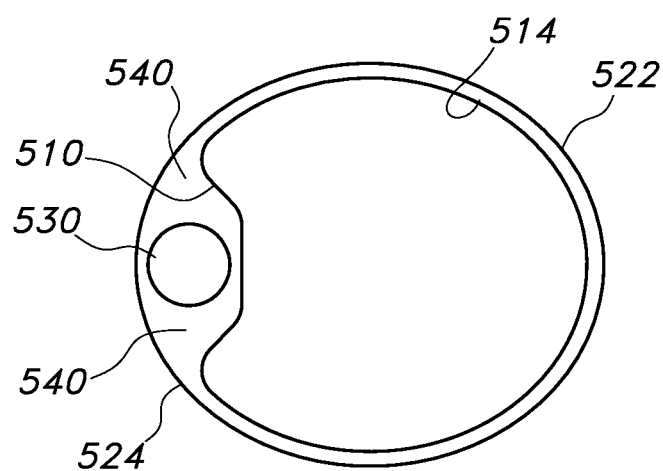
FIG. 15 illustrates blood leakage or a "gutter" around a chimney graft.

FIG. 15 is a cross-sectional view of the main artery 522 having a main graft 510 and the chimney graft or stent-graft 530. While substantial portions of the main graft wall 514 is disposed against substantial portions of the arterial wall 524 of the main artery 522, there are portions 540 of the artery between the main graft 510 and the chimney graft or stent-graft 530 that permit undesirable blood flow or fluid communication there through. These portions 540 are often referred to as "gutters". Such "gutters" are typical of known chimney grafts and main graft combinations and/or as proposed in literature.

The chimney grafts of the present invention prevent the "gutter" problems associated with other devices, including known "chimney" grafts. Details of the chimney grafts of the present invention are described below in conjunction with FIGS. 16-31. These embodiments of the present invention contain gutter-sealing devices to prevent fluid (blood) flow and/or leakage within a main artery among a deployed chimney graft, a deployed main graft, and the wall of the main artery. For example, contain gutter-sealing devices of the present invention may occupy space with the main artery to prevent fluid (blood) flow and/or leakage within the main artery between the deployed chimney graft and the deployed main graft, and/or between the deployed chimney graft and the wall of the main artery, and/or between the deployed main graft and the wall of the main artery, and combinations thereof.

Figure 16:
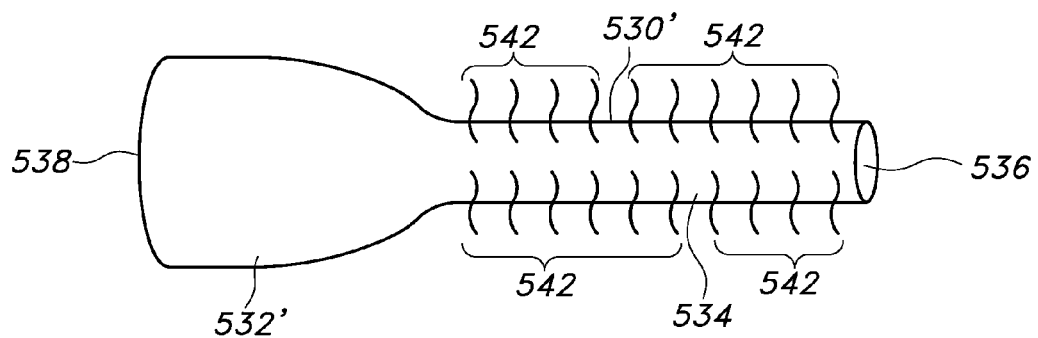
FIG. 16 depicts an embodiment of a chimney graft having a gutter-sealing device in the form of elongate graft tabs according to the present invention.

FIG. 16 depicts a chimney graft 530' of the present invention. The chimney graft 530' may have an enlarged or outwardly flared distal portion 532 of chimney graft 530'. Such an enlarged or outwardly flared distal portion 532' of chimney graft 530' is useful for, among other things, for sealing and anchoring the distal portion 532' of the chimney graft 530' within branched artery 526. The enlarged or outwardly flared distal portion 532' of chimney graft 530' may be from about 10% to about 20% larger in diameter than the nominal diameter of the branched artery 526. The remaining portions or proximal portion 534 of the chimney graft 530' may be about the same size or diameter of the branched artery 526. These dimensions are non-limiting and other dimensions may suitably be used. The chimney graft 530' also an open distal end 538 and an opposed open proximal end 536.

The diameter of the proximal portion 534 of the chimney graft or stent-graft 530' is configured so the main graft or stent-graft 510 does not have to seal against a graft larger than necessary. In other words, diameter of the proximal portion 534 of the chimney graft or stent-graft 530' is configured to ensure adequate blood flow to the branched artery 526 while minimizing its overall profile or diameter. Typically, the diameter of the proximal portion 534 of the chimney graft or stent-graft 530' is about the diameter of the branched artery 526. Moreover, the proximal portion 534 of the chimney graft or stent-graft 530' should be sufficiently stiff or have sufficient radial force to limit or minimize crushing or undesirable deformation. The proximal portion 534 of the chimney stent-graft 530' may include a helical nitinol stent wire configuration, including configurations described herein, to allow for extensibility and fatigue resistance.

To address and solve the problem of gutters, the chimney graft or stent-graft 530' may include a gutter-sealing device in the form of the elongate strips or projections 542 of graft material as depicted in FIG. 16. The elongate strips or projections 542 of graft material may be made from any suitable graft material useful for promoting thrombosis. Suitable graft materials may include any useful biocompatible polymeric materials including, but not limited to, polyesters, polyethylene terephthalate, naphthalene dicarboxylate derivatives such as polyethylene naphthalate, polybutylene naphthalate, polytrimethylene naphthalate, trimethylenediol naphthalate, polytetrafluoroethylene, polyethylene and polypropylene, among others. The elongate strips or projections 542 may be secured to the wall of the chimney graft or stent-graft 530' or may be formed integrally with the wall of the chimney graft or stent-graft 530'. The number and dimensions of the elongate strips or projections 542 of graft material should be sufficient to promote thrombosis thereby sealing the gutter portions 540 associated with known chimney grafts and main grafts.

Figure 17:
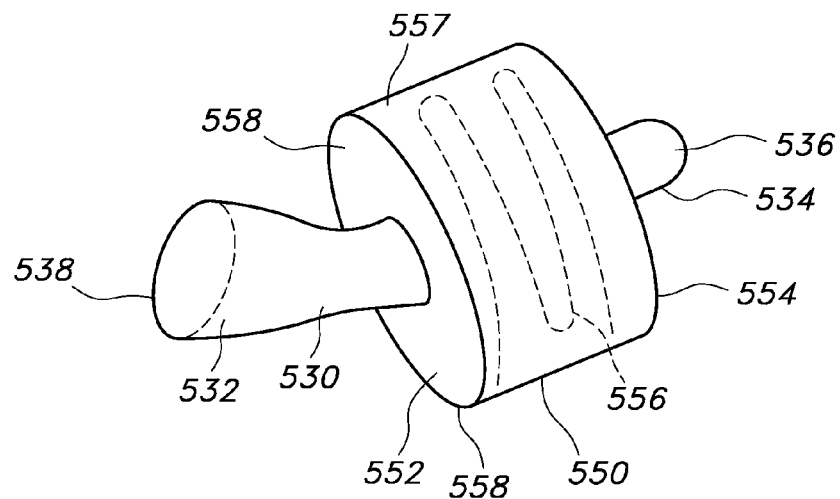
FIGS. 17-19 depict an embodiment of a chimney graft having a gutter-sealing device in the form of a second or sandwich wing graft according to the present invention.
Figure 18:
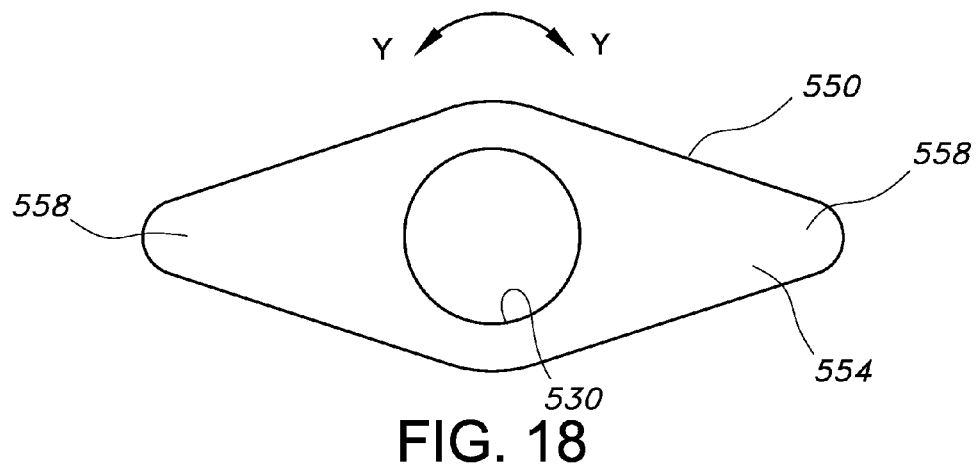
Figure 19:
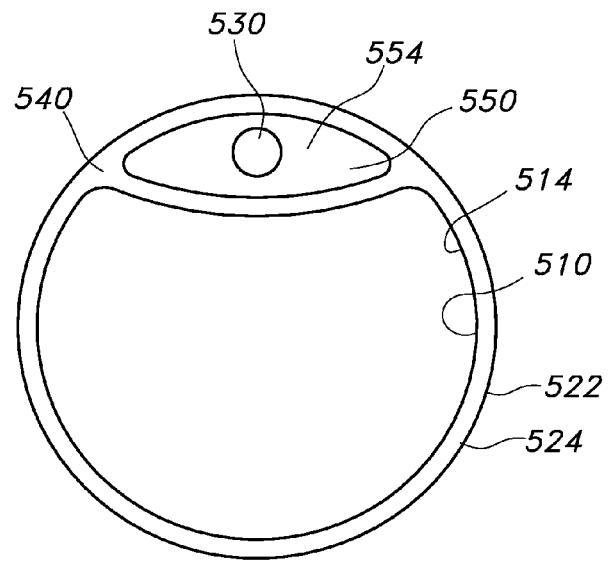

FIGS. 17-19 depict another embodiment for the problem of minimizing and/or eliminating gutters 540 within a main artery 522 between a chimney graft 530 and a main graft 510. The chimney graft 530 may include a gutter-sealing device in the form of a second graft or sandwich wing 550 as a separate piece or member from the chimney graft 530. As depicted in FIG. 18, the second graft or sandwich wing 550 is circumferentially rotatable about the chimney graft 530 as shown by the partial circumferential axis Y-Y. As depicted in FIG. 19, the circumferential rotating feature of the second graft or sandwich wing 550 allows for the elongate wing portions 558 of the second graft or sandwich wing 550 to align with the perimeter of the main graft 510, thereby minimizing or eliminating the gutters 540 associated with known chimney grafts and main grafts. The elongate wing portions are depicted as opposed atraumatic side portions, capable of achieving curved or rounded configurations.

The second graft or sandwich wing graft 550 includes a support frame 556 and a cover 557 for the support frame 556. The support frame 556 may be a metallic support frame, for example a nitinol support frame. Thin nitinol wire, for example 0.005 to 0.007 inches in diameter, may be wound on a shaped mandrel (not shown) to form the support frame 556. The cover 557 over the support frame 556 may be a polytetrafluoroethylene cover or other suitable graft material cover. The distal end 552 of the second graft or sandwich wing 550 is a closed end structure, typically closed off with polytetrafluoroethylene or other suitable graft material to prevent fluid flow thereat. The opposed proximal end 554 of the second graft or sandwich wing 550 may be an open end structure or a closed end structure. In the case of an open end for the proximal end 554, blood pressure can create a "windsock" effect to provide an overall sealing effect for the second graft or sandwich wing 550. Alternatively, the proximal end 554 may be a closed end structure, typically closed off with polytetrafluoroethylene or other suitable graft material to prevent fluid flow thereat.

By allowing the second graft or sandwich wing 550 to rotate around the chimney graft 530, the sandwich wing 550 will self-align into a position between the main graft 510 and the vessel or artery wall 524. A mild interference fit of the second graft or sandwich wing 550 and the chimney graft 530 will keep these two members together, yet still allow for rotation. The chimney graft 530 may have a modest distal and proximal flare (not shown) to capture or maintain the rotating wing 550 between the two flared portions.

Figure 20:
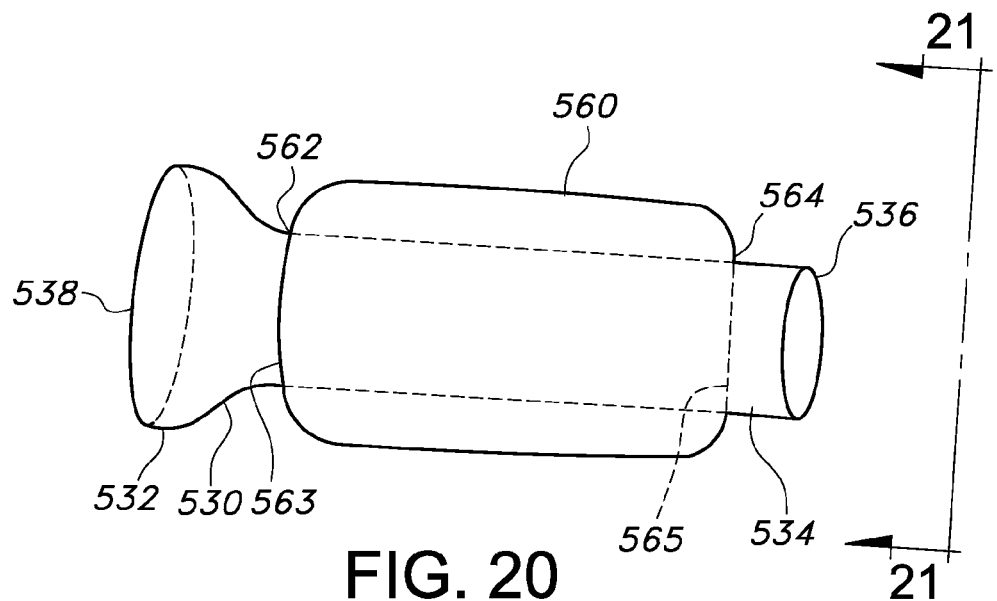
FIGS. 20-24 depict embodiments of a chimney graft having gutter-sealing devices in the forms of concentric grafts or stent-grafts according to the present invention.
Figure 21:
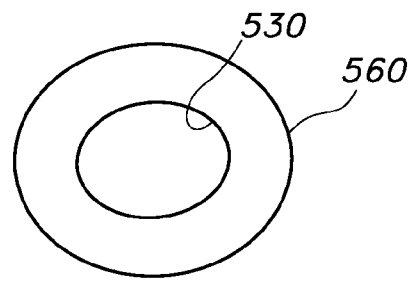
Figure 22:
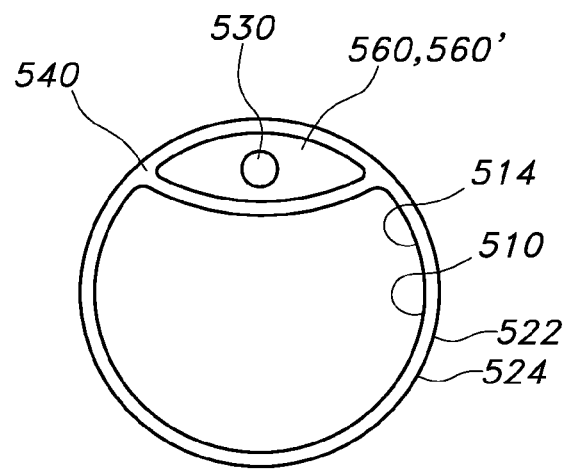

FIGS. 21-22 depict another embodiment of the present invention for the problem of minimizing and/or eliminating gutters 540 within a main artery 522 between a chimney graft 530 and a main graft 510. As depicted in FIGS. 20 and 21, the chimney graft 530 may include a gutter-sealing device in the form of a concentric stent-graft 560 concentrically disposed about the proximal portion 534 of chimney graft 530. The radial extent or diameter of the concentric stent-graft 560 is larger than the radial extent or diameter of the proximal portion 534 of chimney graft 530. The distal end 562 of concentric stent-graft 560 is secured to the proximal portion 534 of chimney graft 530 located towards the distal portion 532 of chimney graft 530 at a distal joint 563, and the proximal end 564 of concentric stent-graft 560 is secured to the proximal portion 534 of chimney graft 530 located towards the proximal end 536 of chimney graft 530 at a proximal joint 565. The distal joint 563 and the proximal joint 565 may be formed by any suitable techniques, including, but not limited to, adhesive bonding, lamination, pressure bonding, thermal bonding and combinations thereof.

The concentric stent-graft 560 has a relatively soft radial force as compared to the main graft or stent-graft 510 so it is partially crushed or partially deformed by the main graft or stent-graft 510. Despite such partial crushing or partial deformation of the concentric stent-graft 560, the chimney graft 530 has sufficient radial force or radial strength to retain its generally cross-section.

As depicted in FIG. 22, the partial crushing or partial deformation of the concentric stent-graft 560 allows the concentric stent-graft 560 to easily fill the space of the gutters 540 associated with known chimney grafts. Use of the concentric stent-graft 560 does not require rotating of the concentric stent-graft 560 about the chimney graft 530, but rather deformability of the concentric stent-graft 560 allows it to easily conform to the "gutter" space, thereby providing a fluid-tight or blood-tight, including substantially fluid-tight or substantially blood-tight, chimney graft and main graft assembly.

Figure 23:
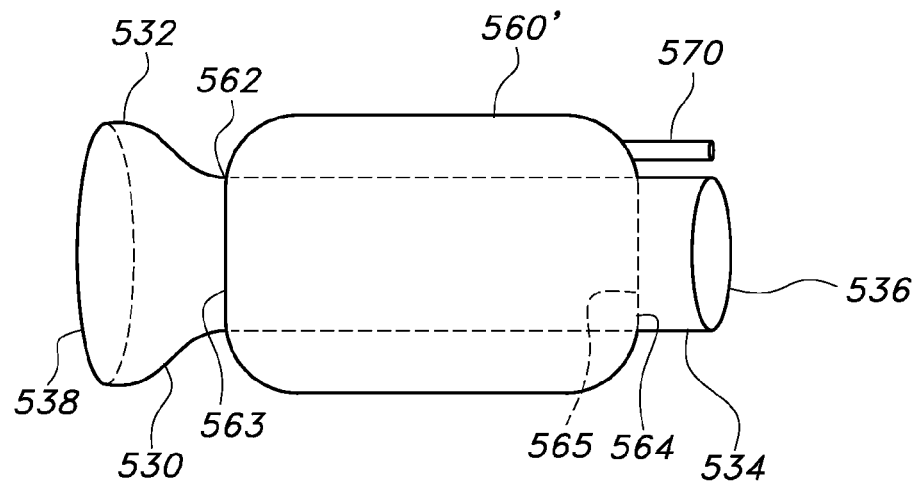

As depicted in FIG. 23, a gutter-sealing device in the form of a concentric graft or stent-graft 560' having a fill port 570 for the introduction of any of the above-described inflation materials is shown. As such the concentric graft or stent-graft 560'may be described as a polymer, i.e., inflation material, fillable or inflatable exterior lumen which is capable of occluding the gutters after deployment of the main graft 510 and the chimney graft 530. The concentric graft or stent-graft 560' acts as an inflatable sealing ring to avoid the gutters associated with known chimney grafts and main grafts.

Figure 24:
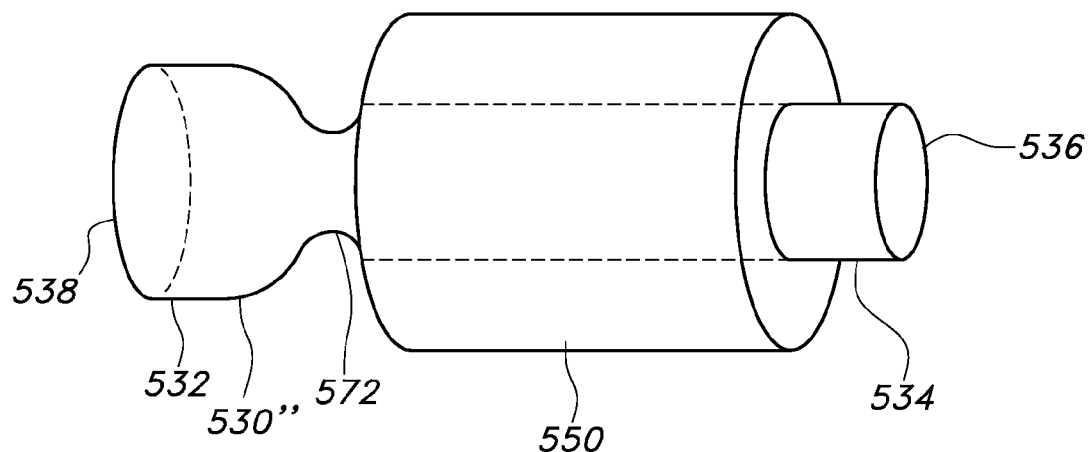

As depicted in FIG. 24, the chimney graft 530" may include section 572 which permits twisting of the chimney graft 530". The section 572 may be configured to allow twisting of the proximal end 536 of chimney graft 530" up to about 90° relative to the distal end 538 of chimney graft 530". In such a case the chimney graft or stent-graft 530" may contain a spiral stent (not shown) with creased polytetrafluoroethylene (not shown) to permit such twisting. The degree of 90° twisting is non-limiting and other degrees or extends of twisting may suitably be used. FIG. 24 depicts the twistable chimney graft 530" with the use of the wing 550. In such a case the wing 550 need not be rotatable or may be just partially rotatable. The twistable chimney graft 530" is not limited to the use of the wing 550 to address the gutter problems associated with known chimney grafts and main grafts. Any of the gutter-sealing device described herein may suitable be used with the twistable chimney graft 530".

Figure 25:
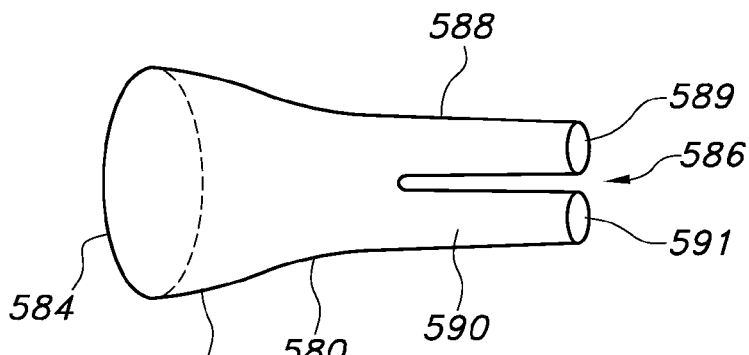
FIGS. 25-29 depict embodiments of a chimney graft having gutter-sealing devices in the forms of bifurcated structures according to the present invention.
Figure 26:
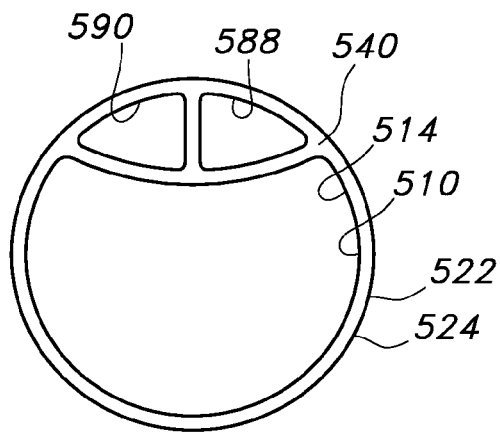

FIGS. 25-26 depict another embodiment of the present invention for the problem of minimizing and/or eliminating gutters 540 within a main artery 522 between a chimney graft 580 and a main graft 510. The chimney graft 580 may have an enlarged or outwardly flared distal portion 582 of chimney graft 580. Such an enlarged or outwardly flared distal portion 582 of chimney graft 580 is useful for, among other things, for sealing and anchoring the distal portion 582 of the chimney graft 580 within branched artery 526. The chimney graft 580 an open distal end 584 and a proximal end 586 two open proximal ends 589, 591. The proximal portions 588, 590 of the chimney graft 580 are separate bifurcated legs of the chimney graft 580. While two legs are illustrated in FIG. 25, additional legs, i.e., three or more, may be used.

As depicted in FIG. 26, proximal portions or legs 588, 590 of the chimney graft 580 may be configured as opposed D-shaped members, either as formed and/or as deployed, with the "straight" portions of the D-shaped being adjacently juxtaposed to prevent fluid flow therein between. The "back-to-back" proximal portions of the legs 588, 590 are stiffer than the remaining portions of the legs 588, 590, thereby resisting crushing and forming a double wall and forcing the two legs to better conform, especially on the edges, to one and the other.

The remaining or non-D-shaped portions of the proximal portions or legs 588, 590 of the chimney graft 580 are deformable to substantially fill any potential gutter areas between the main graft 510 and the chimney graft 582, thereby providing a gutter-sealing device which avoids gutter of leakage problems associated with known chimney grafts and main grafts. The legs 588, 590 will self-align upon deployment thereby forming the illustrated D-shaped configuration. As the legs 588, 590 are long enough and flexible enough, so that orientation control during deployment is not critical, as the legs 588, 590 will self-align. Further, the legs 588, 590 could be crescent shaped with an optional septum as a support with the ability to twist.

Thus, the bifurcated chimney graft 580 will have parallel legs 588, 590 that will juxtaposingly self-align against the lumen wall 524 to minimize or eliminate gutter leakage problems associated with known chimney grafts and main grafts.

Figure 27:
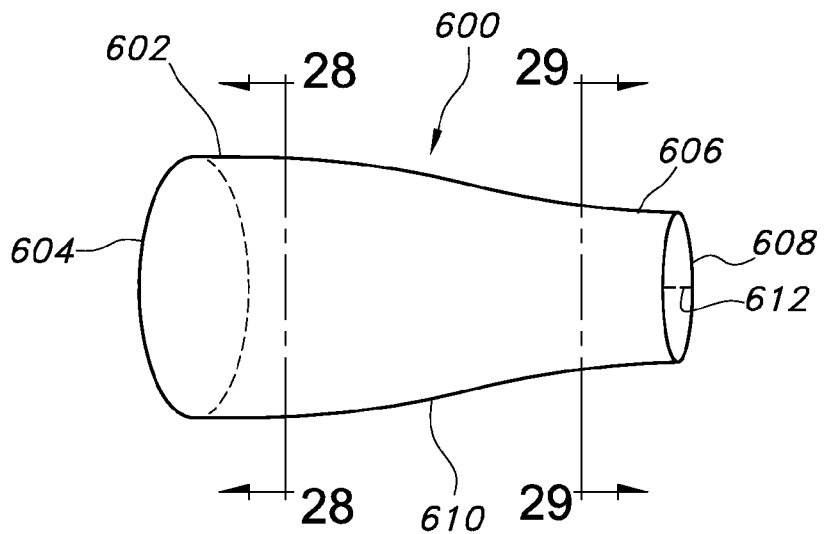
Figure 28:
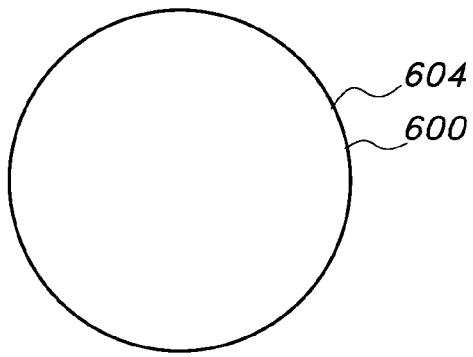
Figure 29:
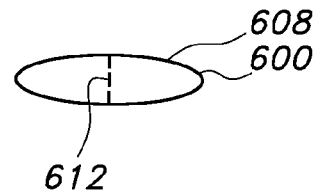

FIGS. 27-29 depict another embodiment of the present invention for the problem of minimizing and/or eliminating gutters 540 within a main artery 522 between a chimney graft 600 and a main graft 510. The chimney graft 600 may have an enlarged or outwardly flared distal portion 602 of chimney graft 600. Such an enlarged or outwardly flared distal portion 602 of chimney graft 600 is useful for, among other things, for sealing and anchoring the distal portion 602 of the chimney graft 600 within branched artery 526. The chimney graft 600 an open distal end 604, which is a substantially circular in shape, as depicted in FIG. 28, to match shape of the branched artery 526.

The chimney graft 600 has a proximal portion 606 with an open proximal end 608. As depicted in FIG. 29, the open proximal end 608 is more oblong or crescent shaped to better match the contours between the main graft 510 and the artery or lumen 510 upon deployment. The chimney graft 600 may transition from a generally circular open distal end 604 to the oblong or crescent shape of the proximal end 608 at transition portion 610. Furthermore, as indicated by the dashed line 612, the proximal portion 606 may be a single lumen of a bifurcated lumen.

Figure 30:
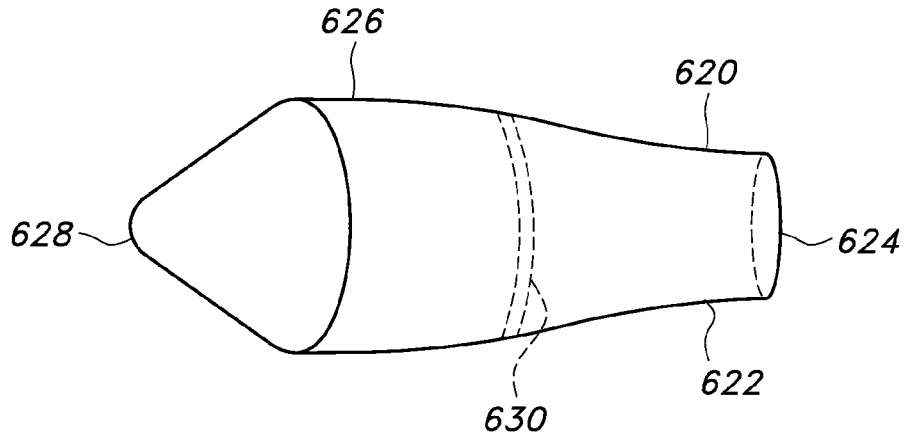
FIGS. 30-31 depict embodiments of a chimney graft having gutter-sealing devices in the forms of a triangular shaped grafts or stent-grafts according to the present invention.
Figure 31:
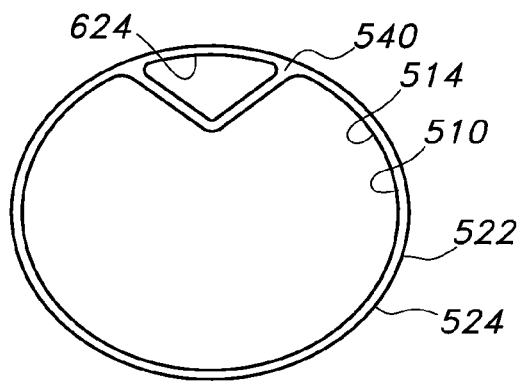

FIGS. 30-31 depict another embodiment of the present invention for the problem of minimizing and/or eliminating gutters 540 within a main artery 522 between a chimney graft 620 and a main graft 510. The chimney graft 620 may have an open triangular-shaped proximal end 628 at its proximal portion 626. The chimney graft 620 may have an open circular distal end 624 at its distal portion 622. The chimney graft 600 may have an enlarged or outwardly flared distal portion 622 (not shown). The triangular-shaped proximal end 626 conforms to the bodily lumen 522 and the gutter space 540 between the chimney graft 620 and the main graft 510. Any useful triangular shape may be used, including an equilateral shape. The corners of the triangular shape should be rounded so as to provide an atraumatic proximal end 628. The graft or stent-graft 620 may be formed on a shaped mandrel (not shown). Moreover, the chimney graft or stent-graft 620 may have a discontinuity 630 to permit the proximal end 628 to flip or twist, e.g., be able to rotate from about 60° to about 120°. This degree of rotation is not limiting, and other amounts of rotation may suitably be used. Thus, the triangular-shaped proximal end 626 may be aligned, including self-aligned, between the main graft 510 and the wall 524 of the main artery 522 to minimize and/or eliminate any gutters 540 within the main artery 522.

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or in the specification may be used with one and another without limitation.

What is claimed is:

1. An endovascular system for deployment at branched arteries comprising:
   a chimney graft having a proximal portion with a proximal open end deployable within a main artery and an opposed distal portion with a distal open end deployable within a branch artery branched from the main artery; and
   a main tubular graft deployable within the main artery and comprising a proximal open end and an opposed open distal end, the proximal and distal ends defining a main tubular graft wall therein between;
   wherein, when deployed, a proximal portion of the main tubular graft wall spans the branch artery; and
   wherein, when deployed, the distal portion of the chimney graft is disposed within the branch artery;
   wherein, when deployed, the proximal portion of the chimney graft is disposed within the main artery such that the proximal end of the chimney graft is about adjacent to or extends beyond the proximal end of the main tubular graft;
   wherein the endovascular system further comprising a gutter-sealing device as being a separate member from the chimney graft
   wherein the gutter-sealing device comprises a second graft disposed over the proximal portion of the chimney graft, the second graft having a wall with opposed elongate atraumatic side wing portions to occupy space within the main artery among the chimney graft, the main tubular graft and wall of the main artery;
   wherein the gutter-sealing device is disposed about at least a portion of the proximal portion of the chimney graft; and
   wherein, during deployment, the second graft is circumferentially rotatable about the proximal portion of the chimney graft so that the second graft is alignable between the main tubular graft and the wall of the main artery to prevent flow of blood among the chimney graft, the main tubular graft and a wall of the main artery.

2. The endovascular system of claim 1 wherein the main tubular graft is an inflatable graft having a proximal circumferential inflatable cuff for sealing the main tubular graft around at least a portion of wall of the main artery.

3. The endovascular system of claim 1 wherein the main tubular graft further comprises a stent.

4. The endovascular system of claim 1 wherein the chimney graft further comprises a stent.

5. The endovascular system of claim 1 wherein the second graft further comprises a closed distal end and an opposed proximal end.

6. The endovascular system of claim 5 wherein the opposed proximal end of the second graft is an open end.

7. The endovascular system of claim 5 wherein the opposed proximal end of the second graft is closed.

8. The endovascular system of claim 5 wherein the wall of the second graft further comprises a metallic support frame disposed within, under or over the wall of the second graft.

* * * * *